United States Patent
Meyer et al.

(10) Patent No.: US 6,682,927 B2
(45) Date of Patent: Jan. 27, 2004

(54) METHODS AND APPARATUS FOR THE HIGH THROUGH-PUT DETECTION OF BINDING INTERACTIONS IN VIVO

(75) Inventors: Tobias Meyer, Menlo Park, CA (US); Mary N. Teruel, Menlo Park, CA (US)

(73) Assignees: Duke University, Durham, NC (US); The Board of Trustees of the Leland Stanford Junior University, Palo Alto, CA (US)

( * ) Notice: Subject to any disclaimer, the term of this patent is extended or adjusted under 35 U.S.C. 154(b) by 195 days.

(21) Appl. No.: 09/826,682

(22) Filed: Apr. 5, 2001

(65) Prior Publication Data

US 2002/0076729 A1 Jun. 20, 2002

Related U.S. Application Data

(63) Continuation-in-part of application No. PCT/US99/19696, filed on Aug. 31, 1999.
(60) Provisional application No. 60/103,092, filed on Oct. 5, 1998, and provisional application No. 60/216,282, filed on Jul. 6, 2000.

(51) Int. Cl.[7] .............................................. C12M 1/34
(52) U.S. Cl. ...................... 435/288.7; 435/7.1; 435/7.8; 435/287.1
(58) Field of Search ..................... 435/7.1, 7.8, 287.1, 435/288.7

(56) References Cited

U.S. PATENT DOCUMENTS

| | | |
|---|---|---|
| 3,604,927 A | 9/1971 | Hirschfeld |
| 3,975,084 A | 8/1976 | Block |
| 5,017,009 A | 5/1991 | Schutt et al. |
| 5,143,854 A * | 9/1992 | Pirrung et al. .............. 436/518 |
| 5,633,724 A | 5/1997 | King et al. |
| 5,677,196 A * | 10/1997 | Herron et al. .............. 436/518 |
| 5,754,514 A | 5/1998 | Guerra |
| 5,774,221 A | 6/1998 | Guerra |
| 5,989,835 A | 11/1999 | Dunlay et al. |
| 6,251,688 B1 * | 6/2001 | Erb et al. .................. 436/518 |

OTHER PUBLICATIONS

Mitsuda, et al.; *Transcriptional regulation of the mouse presenilin–1 gene*, J. Bio. Chem., vol. 272, No. 38, pp. 23489–23497, Database GenBank on LOCUS, GenBank Accession No. AF007560 (Jun. 09, 1997).

Sherrington, R., et al., *Cloning of a gene bearing missence mutations in early–onset familiar Alzheimer's disease*, Nature, vol. 375, pp. 754–760 (Jun. 29, 1995).

Mitsuda, Noriaki, et al., *Transcriptional Regulation of the Mouse Presenilin–1 Gene*, The Journal of Biological Chemistry, vol. 272, No. 38, pp. 23489–23497 (Sep. 19, 1997).

* cited by examiner

*Primary Examiner*—David A. Redding
(74) *Attorney, Agent, or Firm*—Myers Bigel Sibley & Sajovec, PA

(57) ABSTRACT

An apparatus for screening for translocation of a first protein of interest in vivo in a plurality of cells comprises (a) a thin unitary total internal reflection member having a surface portion, (b) a plurality cell contacted to said surface portion by the plasma membrane of said cell, said cell containing said first protein of interest, the protein of interest having a fluorescent group conjugated thereto; (c) a light source operatively associated with the total internal reflection member and positioned for directing a source light into the member to produce an evanescent field adjacent the surface portion, with the evanescent field extending into a first portion of the cell adjacent the plasma membrane, the evanescent field being weaker in a second portion of the cell, the fluorescent group emitting light when in the first portion of the cell and emitting less light when in the second portion of the cell; (d) coupling means for coupling the light source to the thin unitary total internal reflection member and illuminate at least 10 square millimeters of the surface portion; and (e) a light detector operatively associated with the total internal reflection member and configured to detect emitted light from the cells, whereby the emission of more or less light from the cell indicates the translocation of the protein between the first and second portions of the cell.

31 Claims, 10 Drawing Sheets

METHODS AND APPARATUS FOR THE HIGH THROUGH-PUT DETECTION OF BINDING INTERACTIONS IN VIVO

RELATED APPLICATIONS

This application claims the benefit of provisional application serial No. 60/216,282, filed Jul. 6, 2000, the disclosure of which is incorporated by reference herein in its entirety, and this application is also a continuation-in-part of PCT application PCT/US99/19696, filed Aug. 31, 1999 which was published in English under Article 21(2), and in turn claims the benefit of provisional application No. 60/103,092, filed Oct. 5, 1998, the disclosures of both of which are incorporated by reference herein in their entirety.

GOVERNMENT SUPPORT

This invention was made with Government support under National Institutes of Health grants RO1GM-51457, R21CA-83229, GM-48113, GM-51457, and 1F32NS10767. The Government has certain rights to this invention.

FIELD OF THE INVENTION

The present invention concerns method and apparatus for detecting binding interactions in cells. The methods and apparatus are particularly suitable for the high through-put screening of cell arrays and combinatorial libraries.

BACKGROUND OF THE INVENTION

A significant fraction of known cellular signaling proteins have been shown to translocate to or dissociate from the plasma membrane as part of their activation cycle. In particular, the recruitment of cytosolic proteins by activated receptors and plasma membrane signaling proteins is a general principle in receptor-mediated signal transduction (Pawson, T. (1995) *Nature* 373, 573–580; Ullrich, A. & Schlessinger, J. (1990) *Cell* 61, 203–212; Pfister, et al. (1985) *Science* 228, 891–893; Hunter, T. (1987) *Cell* 50, 823–829; Pawson, T. & Scott, J. D. (1997) *Science* 278, 2075–2080). Translocation is often transient with active signaling components dissociating from the plasma membrane and acting on cytosolic and nuclear targets. Recruitment processes are exemplified by the binding of cytosolic SH2-domain containing proteins to tyrosine phosphorylated plasma membrane receptors (Koch, et al. (1991) *Science* 252, 668–674; Kypta, et al. (1990) *Cell* 62, 481–492) and by the binding of cytosolic signaling enzymes to GTP bound small G-proteins at the plasma membrane (Moodie, et al. (1993) *Science* 260, 1658–1661; Stokoe, et al. *Science* 264, 1463–1467; Leevers, et al. (1994) *Nature* 369, 411–414). In addition to direct recruitment by protein-protein binding interactions, protein-lipid binding interactions are also important for translocation (Nishizuka, Y. (1992) *Science* 258, 607–614; Rameh, L. E. & Cantley, L. C. (1999) *J. Biol. Chem.* 274, 8347–8350). Lipid recruitment is exemplified by the translocation of PH-domain containing proteins in response to receptor-mediated production of plasma membrane phosphatidylinositol lipids (Ferguson, et al. (1995) *Cell* 83, 1037–1046), C1-domain containing proteins in response to plasma membrane diacylglycerol production, and C2-domain containing proteins in response to calcium mediated binding interactions with negatively charged lipids in the plasma membrane (Nishizuka, Y. (1992) *Science* 258, 607–614; Newton, A. C. (1995) *Curr. Biol.* 5, 973–976).

Why does translocation to the plasma membrane play such a ubiquitous role in signal transduction? First, most of the cellular interactions with the extracellular environment are mediated by receptors located in the plasma membrane. Activated receptors often serve as a scaffold for signaling proteins that have to be recruited for a particular signaling function. Second, plasma membrane translocation concentrates signaling proteins at the membrane and enhances the frequency of intermolecular collisions. Translocation then serves as an intermediate signaling step that enhances the effective on-rate for target binding or the Michaelis constant for enzyme action (Haugh, J. M. & Lauffenberger, D. A. (1997) *Biophys. J.* 72, 2014–2031).

Over the last few years, confocal imaging measurements were used to monitor the plasma membrane translocation of signaling proteins over time (Sakai, et al. (1997) *J. Cell Biol.* 139, 1465–1476; Venkateswarlu, et al. (1998) *Curr. Biol.* 8, 463–466; Barak, et al. (1997) *J. Biol. Chem.* 272, 27497–27500; Oancea, et al. (1997) *J. Cell Biol.* 140, 485–498; Stauffer, T. & Meyer, T. (1997) *J. Cell Biol.* 139, 1447–1454; Stauffer, et al. (1998) *Curr. Biol.* 8, 343–346; Kontos, et al. (1998) *Mol. Cell Biol.* 18: 4131–4140; Oancea, E. & Meyer, T. (1998) *Cell* 95, 307–318; Parent, et al. (1998) *Cell* 95, 81–91; Meili, et al. (1999) *EMBO J.* 18, 2092–2105; Watton, S. J. & Downward, J. (1999) *Curr. Biol.* 9, 433–436). Although successful for many proteins, this approach was limited to cell types where the confocal resolution was sufficient to separate the plasma membrane from the cytosol and where the translocation involved a significant fraction of the cytosolic protein. Nevertheless, these imaging studies showed that single cell time-course measurements of translocation events can give important insights into the activation mechanism of enzymes (Oancea, E. & Meyer, T. (1998) *Cell* 95, 307–318), into spatial gradients of second messengers (Parent, et al. (1998) *Cell* 95, 81–91; Meili, et al. (1999) *EMBO J.* 18, 2092–2105; Watton, S. J. & Downward, J. (1999) *Curr. Biol.* 9, 433–436) and into the single cell kinetics of specific signaling steps (Stauffer, T. & Meyer, T. (1997) *J. Cell Biol.* 139, 1447–1454; Oancea, E. & Meyer, T. (1998) *Cell* 95, 307–318).

Biomolecular or combinatorial arrays have provided a means for the high throughput screening of chemical libraries. See, e.g., U.S. Pat. No. 5,143,854. A variety of specific techniques for carrying out the automated screening of such arrays have been developed, including the evanescent scanning of a pixel array. See U.S. Pat. No. 5,633,724.

A disadvantage of combinatorial arrays is that they provide an in vitro rather than an in vivo assay. In vitro binding assays can seldom provide an accurate measure of how binding will actually occur in vivo, particularly for intracellular binding events, because the complexity of the intracellular environment is difficult to replicate outside of the cell. Of course, the ultimate application of many screening assays is to develop in vivo applications for the compounds being screened. Accordingly, there is a continued need for new in vivo screening techniques that can be readily adapted to automated or high throughput screening.

SUMMARY OF THE INVENTION

A first aspect of the present invention is an apparatus for screening for translocation of a first protein of interest in vivo in a cell. The apparatus comprises:
(a) a total internal reflection member having a surface portion. If desired, the surface portion can be divided into separate and discrete segments.
(b) A cell contacted to the surface portion by the plasma membrane of the cell, the protein having a fluorescent group conjugated thereto. If desired, different cells can be contacted to different ones of the separate and discrete segments.

(c) A light source operatively associated with the total internal reflection member and positioned for directing a source light into the member to produce an evanescent field adjacent the surface portion, with the evanescent field extending into a first portion of the cell adjacent the plasma membrane, with the evanescent field being weaker in a second portion of the cell, the fluorescent group emitting light when in the first portion of the cell and emitting less light when in the second portion of the cell (i.e., less light as compared to the amount emitted when the same fluorescent group is in the first portion of the cell).

(d) A light detector operatively associated with the total internal reflection member and configured to detect emitted light from the cell The emission of more or less light from the cell indicates the translocation of the first protein between the first and second portions of the cell.

The cell or cells may further contain a second protein of interest located in either the first portion of the cell or the second portion of the cell, whereby the emission of more or less light from the cell indicates the presence or absence of specific binding between the first and second proteins of interest. When the second protein is located in the first portion of the cell, the emission of more light indicates the specific binding of the proteins of interest, and the emission of less light indicates the lack of such binding. When the second protein is located in the second portion of the cell, the emission of less light indicates the specific binding of the proteins of interest, and the emission of more light indicates the lack of such binding. First and second proteins of interest may be members of a specific binding pair. Either or both of the first and second proteins of interest may be expressed by a nucleic acid carried by the cell; either of the first and second proteins of interest may be a member of a library of compounds, with a different member of said library being expressed in cells of different segments, while the other protein of interest is the same in the cells of different segments, to provide a way to rapidly screen the library of compounds.

A second aspect of the present invention is a method of detecting translocation of a first protein of interest within a cell. The method comprises:

(a) providing a total internal reflection member having a surface portion, with a cell contacted to the surface portion by the plasma membrane of the cell;

(b) directing a source light into the member to produce an evanescent field adjacent the surface portion, with the evanescent field extending into a first portion of the cell adjacent the plasma membrane, the evanescent field being weaker in a second portion of the cell; wherein the protein of interest has a fluorescent group conjugated thereto; the fluorescent group emitting light when in the first portion of the cell and emitting less light when in the second portion of the cell; and then (c) detecting emitted light from the fluorescent group, with the emission of more or less light from the fluorescent group indicating the translocation of the first protein of interest between the first and second portions of the cell.

The method may be used with a second protein of interest as described in connection with the apparatus above. An analysis of a test compound (e.g., a member of a library of compounds as described below) may be carried out by administering a test compound to the cell to determine whether or not said test compound disrupts the binding of said first and second proteins of interest. The analysis may be made a quantitative analysis by repeating steps (a) through (c) with different cells at different concentrations of said test compound. The degree of binding or disruption of binding may then be determined at different concentrations of the test compound.

The methods and apparatus of the invention can be used on individual cells or for screening multiple cell populations, or libraries of cells or libraries of compounds, as described in greater detail below.

A further aspect of the present invention is a method of screening binding between a first protein of interest and a library of second proteins of interest within a plurality of cells. The method comprises:

(a) providing a total internal reflection member having a surface portion, the surface portion having a plurality of separate and discrete segments, with a cell contacted to each of the surface portion segments by the plasma membrane of the cells;

(b) directing a source light into the member to produce an evanescent field adjacent the surface portion, with the evanescent field extending into a first portion of the cell adjacent the plasma membrane, the evanescent field being weaker in a second portion of the cell; wherein one of the proteins of interest has a fluorescent group conjugated thereto, and the other of the proteins of interest is located in either the first portion of the cell or the second portion of the cell; and wherein one of the proteins of interest is the same in each of the cells; and the other of the proteins of interest is a different member of the library in cells contacted to different segments; with the fluorescent group emitting light when in the first portion of each of the cells and emitting less light when in the second portion of each of the cells; and then (c) detecting emitted light from each of the segments, with the presence or absence of emitted light indicating the presence or absence of specific binding between the proteins of interest in the cell in each of the segments.

A further aspect of the present invention is a method of screening a library of compounds for the ability to disrupt binding between first and second proteins of interest. The method comprises:

(a) providing a total internal reflection member having a surface portion, the surface portion having a plurality of separate and discrete segments, with a cell contacted to each of the surface portion segments by the plasma membrane thereof;

(b) directing a source light into the member to produce an evanescent field adjacent the surface portion, with the evanescent field extending into a first portion of the cell adjacent the plasma membrane, the evanescent field being weaker in a second portion of the cell;
wherein one of the proteins of interest has a fluorescent group conjugated thereto, and the other of the proteins of interest is located in either the first portion of the cell or the second portion of the cell;
the fluorescent group emitting light when in the first portion of each of the cells and emitting less light when in the second portion of each of the cells; then (c) administering a different member of the library of compounds to each of the separate and discrete segments (e.g., by contacting a different compound to the cells, or by expressing a different compound from a different nucleic acid in each of said cells); and then (d) detecting emitted light from the fluorescent group in the cells from each of the separate and discrete segment.

The presence or absence of emitted light from the fluorescent group indicates the disruption or lack of disruption of specific binding between the proteins of interest by the member of the library administered to the segment.

When screening libraries, the screening steps may be repeated with different members of the library until sufficient members of the library have been screened. It will also be appreciated that each cell may contain or be administered a sub-population or subpool of the library, and that where a population or subpopulation is found to contain a compound having desired properties, the screening step may be repeated with additional subpopulations containing the desired compound until the population has been reduced to one or a sufficiently small number to permit identification of the compound desired.

A further aspect of the present invention is an apparatus for screening for translocation of a first protein of interest in vivo in a cell. The apparatus comprises:

(a) a thin unitary total internal reflection member having a surface portion. If desired, the surface portion can be divided into separate and discrete segments. The total internal reflection member is preferably a single thin member which can be conveniently formed from a microscope slide coverslip, although other embodiments are also contemplated.

(b) A cell (typically a plurality of cells) contacted to the surface portion by the plasma membrane of the cell, the protein having a fluorescent group conjugated thereto. If desired, different cells can be contacted to different ones of the separate and discrete segments.

(c) A light source operatively associated with the total internal reflection member and positioned for directing a source light into the member to produce an evanescent field adjacent the surface portion, with the evanescent field extending into a first portion of the cell adjacent the plasma membrane, with the evanescent field being weaker in a second portion of the cell, the fluorescent group emitting light when in the first portion of the cell and emitting less light when in the second portion of the cell (i.e., less light as compared to the amount emitted when the same fluorescent group is in the first portion of the cell).

(d) coupling means such as a cylindrical lens or lenses, or a focused laser used in combination with a one-dimensional scanning mirror, etc., for coupling the light source to the thin unitary total internal reflection member, preferably thereby providing wide-field illumination of the surface portion of the total internal reflection member.

(e) A light detector operatively associated with the total internal reflection member and configured to detect emitted light from the cell The emission of more or less light from the cell indicates the translocation of the first protein between the first and second portions of the cell.

The cell or cells may further contain a second protein of interest located in either the first portion of the cell or the second portion of the cell, whereby the emission of more or less light from the cell indicates the presence or absence of specific binding between the first and second proteins of interest. When the second protein is located in the first portion of the cell, the emission of more light indicates the specific binding of the proteins of interest, and the emission of less light indicates the lack of such binding. When the second protein is located in the second portion of the cell, the emission of less light indicates the specific binding of the proteins of interest, and the emission of more light indicates the lack of such binding. First and second proteins of interest may be members of a specific binding pair. Either or both of the first and second proteins of interest may be expressed by a nucleic acid carried by the cell; either of the first and second proteins of interest may be a member of a library of compounds, with a different member of said library being expressed in cells of different segments, while the other protein of interest is the same in the cells of different segments, to provide a way to rapidly screen the library of compounds.

A further aspect of the present invention is a method of detecting translocation of a first protein of interest within a cell. The method comprises:

(a) providing a thin unitary total internal reflection member having a surface portion, with a cell contacted to the surface portion by the plasma membrane of the cell;

(b) directing a source light into the member through a coupling means to produce a wide-field evanescent field adjacent the surface portion, with the evanescent field extending into a first portion of the cell adjacent the plasma membrane, the evanescent field being weaker in a second portion of the cell; wherein the protein of interest has a fluorescent group conjugated thereto; the fluorescent group emitting light when in the first portion of the cell and emitting less light when in the second portion of the cell; and then (c) detecting emitted light from the fluorescent group, with the emission of more or less light from the fluorescent group indicating the translocation of the first protein of interest between the first and second portions of the cell.

The method may be used with a second protein of interest as described in connection with the apparatus above. An analysis of a test compound (e.g., a member of a library of compounds as described below) may be carried out by administering a test compound to the cell to determine whether or not said test compound disrupts the binding of said first and second proteins of interest. The analysis may be made a quantitative analysis by repeating steps (a) through (c) with different cells at different concentrations of said test compound. The degree of binding or disruption of binding may then be determined at different concentrations of the test compound.

The methods and apparatus of the invention can be used on individual cells or for screening multiple cell populations, or libraries of cells or libraries of compounds, as described in greater detail below.

The present invention is explained in greater detail in the drawings herein and the specification set forth below.

DETAILED DESCRIPTION OF THE PREFERRED EMBODIMENTS

Definitions

Figure 1:
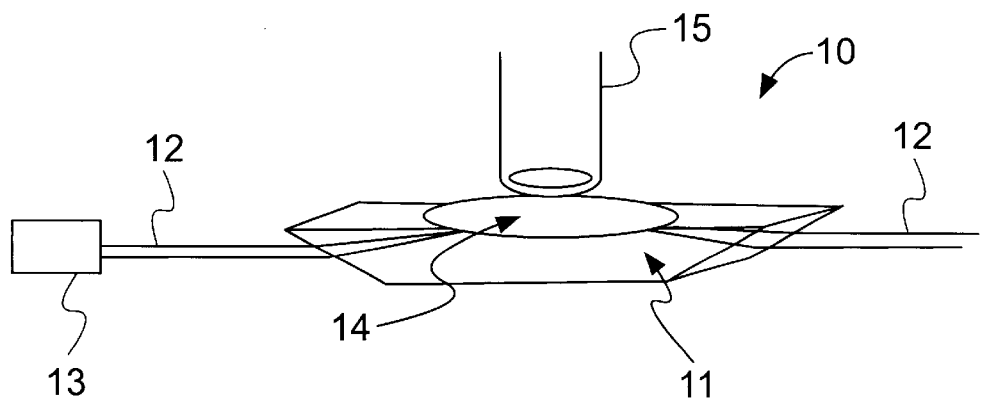
FIG. 1 is a schematic illustration of an evanescent microscope of the invention, useful for carrying out a quantitative translocation analysis (QTA).

The term "contact" or contacted to", when used herein with respect to a cell or cells contacted to a total internal reflection member, means sufficiently close to be excitable by the evanescent wave. This means that, in a typical configuration, the total internal reflection member is less than 5 micrometer away from the cell membrane. Such contact may be direct or indirect through intervening materials (e.g, cell adhesion proteins or extracellular matrix).

Total internal reflection (TIR) members useful for carrying out the present invention include prisms, waveguides, fibers, and specialized microscope objectives. The member may be a single unitary element or a combination of elements (for example, a glass slide contacted to a prism by an intervening oil). In the case of waveguides and fibers, there may be several TIR surfaces. Additionally, the TIR surface can be on an optically transparent substrate surface such as a glass slide, optical film, or the like, that is optically coupled with the TIR element in a conventional manner, for example, using a refractive index matching oil or a compressible optical polymer such as those disclosed by Sjodin, "Optical interface means," PCT publication WO 90/05317, 1990. The substrate surface is preferably removable from the TIR element, and may even be disposable. If the test cell or cells are contacted directly to the TIR element, such as the prism, it may be necessary to clean or replace the prism before testing other cells, and the alignment of the prism will then have to be checked and possibly readjusted. Providing a removable substrate (e.g. by means of refractive index matching oil on, for example, a prism) eliminates or at least greatly reduces the cost and effort involved in ensuring that the prism is clean and aligned.

The TIR members may be present in a variety of shapes and geometries. In one embodiment of the invention, the member may be a single unitary element or a combination of elements (for example, a glass slide contacted to a prism by an intervening oil), but in the instant invention is a preferably a single thin unitary element. In the case of waveguides and fibers, there may be several TIR surfaces. If the test cell or cells are contacted directly to the TIR element, such as the prism, it may be necessary to clean or replace the prism before testing other cells, and the alignment of the prism will then have to be checked and possibly readjusted. Providing a removable substrate (e.g. by means of refractive index matching oil on, for example, a prism) eliminates or at least greatly reduces the cost and effort involved in ensuring that the prism is clean and aligned.

The TIR member may have various dimensions that can be selected by the skilled artisan. Preferably, the thickness of the member range from about 100 to about 5000 micrometers. The width of the member preferably ranges from about 5 or 6 mm to about 300 mm, and the depth of the member preferably ranges from about 5 or 6 mm to about 300 mm. A preferred member is 200 micrometers thick, 22 mm wide and 22 mm deep.

An advantage of coupling the light source directly into a thin unitary TIR element such as a coverslip is the much improved geometry for imaging, and in particular directly into the side or edge of the thin unitary TIR element (e.g., glassplate or coverslip). The excitation pathway is now essentially out of the way from the emission pathway so that an inverted wide-field microscope can be used. Furthermore, since the laser light is reflected several times from the illuminated area during its passage into the coverslip, significantly less laser power is needed to obtain the same overall brightness of illumination.

By "wide field" is meant that an area of the surface portion of the total internal reflection member of at least 10, 15, 20 or 30 square millimeters is effectively illuminated by the light source. Such an area can contain 6, 10, 20 or 30 or more separate and discrete regions, all of which may contain separate and discrete cell populations, e.g., spots on a thin unitary TIR element or wells in a multi-well cell chamber, as well as others.

Light sources suitable for carrying out the present invention include, but are not limited to, lasers, LEDs, coherent frequency-converting devices (an example of which is disclosed by Kozlovsky et at., "Resonator-enhanced frequency doubling in an extended-cavity diode laser," presented at Blue/Green Compact Lasers, New Orleans Feb. 1–5, 1993 and references therein), an array of surface emitting LEDs (Bare et al., "A simple surface-emitting LED array useful for developing free-space optical interconnects," *IEEE, Photon. Tech. Lett.*, Vol. 5, 172–175, 1993), and a suitable array of vertical-cavity surface-emitting lasers (VCSEL) where each polymer array pixel could have its own corresponding laser on the VCSEL array (Salah and Teich, Fundamentals of Photonics, Wiley-Interscience, New York, 1991, p. 638). Examples of molecular tag/light source pairs include CY5/ HeNe laser, CY5/laser diode (e.g. Toshiba TOLD9410(s)), CY5/LED (e.g. Hewlett-Packard HMP8150), fluorescein/ argon ion laser, and rhodamine/argon ion laser.

Any suitable optical coupling means can be used to carry out the present invention, including but not limited to cylindrical lenses, a focussed laser scanned into the TIR by a one-dimensional scanning mirror, etc.

Any suitable light detector may be used to carry out the present invention. An example of a suitable detection system is shown in U.S. Pat. No. 5,633,724 to King et al. As illustrated therein, an imaging system collects and images the optical signal through an optical filter and onto a two-dimensional array detector. Imaging systems can contain lenses or a coherent fiber bundle. The filter is chosen to transmit the optical signal and reject radiation at other frequencies. The detector is preferably a two dimensional detector such as CCD array, image intensified CCD, vidicon or video camera. An optional image intensifier, such as a Hamamatsu V4170U image intensifier, can be used in addition to detector if the optical signal is weak.

Cells used to carry out the present invention are typically eukaryotic cells, which may be yeast, plant, or animal cells. Yeast and animal cells, particularly mammalian cells, are currently preferred. Example plant cells include, but are not limited to, arabidopsis, tobacco, tomato and potato plant cells. Example animal cells include, but are not limited to, human, monkey, chimpanzee, rat, cat, dog, and mouse cells. In one embodiment, each of the cells is adherent to the thin unitary TIR element. Many of the cells are present within a spot (e.g., subregion) or a well in the instance when barriers are used between the populations. For such an embodiment to work properly, it is preferred that the cells adhere directly to the thin unitary TIR element or a coating thereon (e.g., less that about 500 nm away from the surface).

"Detectable groups" or "detectable proteins" used to carry out the present invention include fluorescent proteins, such as green fluorescent protein (GFP) and apoaequorin, including analogs and derivatives thereof. Green fluorescent protein is obtained from the jellyfish *Aequorea victoria* and has been expressed in a wide variety of microbial, plant, insect and mammalian cells. A. Crameri et al., *Nature Biotech.* 14, 315–319 (1996). Any detectable group may be employed, and other suitable detectable groups include other fluorophores or fluorescent indicators, such as a fusion tag with any binding domain such as avidin, streptavidin and ligand binding domains of receptors. Coupling of biotin or other ligands to the fluorophore or indicator of interest may be achieved using a dextran matrix or other linker system. The detectable protein may be one which specifically binds a fluorophore, as in FLASH technology. Fluorescent detectable groups (including both fluorescent proteins and proteins that bind a separate fluorophore molecule thereto) are currently preferred.

"Internal structure" as used herein refers to a separate, discreet, identifiable component contained within a cell. The term "structure" as applied to the constituent parts of a cell is known (see, e.g., R. Dyson, Cell Biology: A Molecular Approach, pg, 10 (2d ed. 1978)), and the term "internal structure" is intended to exclude external structures such as flagella and pili. Such internal structures are, in general, anatomical structures of the cell in which they are contained. Examples of internal structures include both structure located in the cytosol or cytoplasm outside of the nucleus (also called "cytoplasmic structures"), and structures located within the nucleus (also called "nuclear structures"). The nucleus itself including the nuclear membrane are internal structures. Structures located within the cytoplasm outside of the nucleus are currently preferred. Thus the term "internal structure" is specifically intended to include any non-uniformly distributed cellular component, including proteins, lipids, carbohydrates, nucleic acids, etc., and derivatives thereof.

"Library" as used herein refers to a collection of different compounds, typically organic compounds, assembled or gathered together in a form that they can be used together, either simultaneously or serially. The compounds may be small organic compounds or biopolymers, including proteins and peptides. The compounds may be encoded and produced by nucleic acids as intermediates, with the collection of nucleic acids also being referred to as a library. Where a nucleic acid library is used, it may be a random or partially random library, commonly known as a "combinatorial library" or "combinatorial chemistry library", or it may be a library obtained from a particular cell or organism, such as a genomic library or a cDNA library. Small organic molecules can be produced by combinatorial chemistry techniques as well. Thus in general, such libraries comprise are organic compounds, including but not limited oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (that is, oligopeptides) and proteins, oligonucleotides (the term oligonucleotide also referred to simply as "nucleotide, herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. See, e.g, U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

"Nucleic acid" as used herein refers to both DNA and RNA.

"Protein" as used herein is intended to include protein fragments, or peptides. Thus the term "protein" is used synonymously with the phrase "protein or fragment thereof" (for the purpose of brevity), particularly with reference to proteins that are "proteins of interest" or members of a specific binding pair. Protein fragments may or may not assume a secondary or tertiary structure. Protein fragments may be of any length, from 2, 3, 5 or 10 peptides in length up to 50, 100, or 200 peptides in length or more, up to the full length of the corresponding protein.

"Specifically binds" and "specific binding" as used herein includes but is not limited to stereospecific binding, electrostatic binding, or hydrophilic binding interactions. Thus, specifically binds and specific binding are exhibited by at least a two or three fold (or two or three times), greater apparent binding affinity between the binding partners as compared to other proteins or binding partners within the cell in which binding is being detected.

"Specific binding pair" refers to a pair of molecules (e.g., a pair of proteins) that specifically bind to one another. A pair of molecules that specifically bind to one another, which may be the same or different, are referred to as members of a specific binding pair. A protein that is a member of a specific binding pair may be a protein that has been previously determined to be a member of a specific binding pair or a protein that is a putative member of a specific binding pair. Examples of the latter include members of a library, such as the products of a cDNA or combinatorial library, or a protein for which a binding partner has not yet been identified, where it is desired to identify a naturally occurring (e.g., a product of a cDNA or genomic DNA library) or non-naturally occurring (e.g., combinatorial) binding partner therefore.

"Translocation" as used herein refers to a change in distribution of a protein or conjugate (including a fusion protein) from one physical distribution within a cell to another, different, physical distribution within a cell. Preferably, translocation is from either a uniform or non-uniform distribution to a non-uniform distribution. Translocation could also be from a non-uniform to a uniform distribution. Translocation may be induced by any suitable means, such as by administration of a physical or chemical signal (e.g., administration of a compound such as a phorbol ester or platelet activating factor (PAF)). Many signal transduction proteins are known to change their distribution after stimulation of the corresponding receptor (or other appropriate stimulus), and can be used to carry out the present invention. Often these translocation events are mediated by subdomains of such signaling proteins (e.g., the C1 or C2 subdomains), and such subdomains can be used to carry out the present invention.

As noted above, the present invention provides a method of detecting a protein-protein interaction. The method comprises first providing a cell that contains a first heterologous conjugate and a second heterologous conjugate. The first heterologous conjugate comprises a first protein of interest conjugated to a detectable group. The second heterologous conjugate comprises a second protein of interest (which may be the same as or different from the first protein of interest) conjugated to a protein that specifically binds to an internal structure within the cell. The binding of the protein that specifically binds to an internal structure may be immediate, may be induced (as discussed below), or may be a prior binding in the case of a protein that is previously localized to or permanently located at the internal structure of interest. The two conjugates are preferably each present in the cell at a total concentration between about 1 or 10 nM to about 1 or 10 mM.

The presence or absence of binding of the detectable group to the internal structure is then detected, the presence of the binding indicating that the first and second proteins of interest specifically bind to one another. Detection may be by any suitable means depending upon the detectable group employed, but preferably the detectable group is a fluorescent group and detection is carried out by optical or visual reading, which may be done manually, by an automated apparatus, or by combinations thereof.

If desired, the second heterologous conjugate can further comprise a detectable group, which detectable group is preferably different from the detectable group located on the first heterologous conjugate and fluoresces at a different wavelength therefrom. For example, both detectable groups could be a green fluorescent proteins, yet simply different mutants of green fluorescent protein that fluoresce at different wavelengths.

Either or both of the heterologous conjugates may be introduced directly in the cell by any suitable means, such as by electroporation or lipofection. In the alternative, when the heterologous conjugates are fusion proteins, a nucleic acid (typically a DNA) may be stable introduced into the cell (for example, as a plasmid), which nucleic acid includes a suitable promoter segment that controls and causes the expression of a nucleic acid encoding the fusion protein. Again, either or both of the fusion proteins may be produced in the cell in this matter.

Binding events in the instant invention may be direct or indirect binding events. Indirect binding events are those mediated through an intermediate, or bridging, molecule or conjugate. Administration of such a bridge molecule can be a signal to induce translocation (discussed below). For example, the bridging molecule may be a covalent conjugate of FK506 and cyclosporin, to cause the indirect binding of FKBP12 and cyclophilin (both conventionally cytosolic proteins) to one another. Either of the FKBP12 or the cyclophilin can be modified so that it binds to the plasma membrane, such as by lipidating the protein or forming a fusion protein with the transmembrane domain of a transmembrane protein.

Any internal structure as defined above can be used to carry out the present invention, as long as the binding of the detectable group to the internal structure provides a different detectable signal from the cell than when the detectable group is not bound to the internal structure. In one preferred embodiment the internal structure is contained in the cell cytoplasm. Examples of internal structures include, but are not limited to, plasma membrane, cytoskeleton (including but not limited to actin cytoskeleton, tubulin cytoskeleton, intermediate filaments, focal adhesions, etc.), centromere, nucleus, mitochondria, endoplasmic reticulum, vacuoles, golgi apparatus, and chloroplasts. Preferably, the internal structure is either the plasma membrane or cortical cytoskeleton.

In a preferred embodiment of the invention, the protein that specifically binds to an internal structure is a translocatable protein. In this embodiment, the method further comprises the step of inducing translocation of the second heterologous conjugate prior to the detecting step. Induction of translocation may be carried out by any suitable means, such as by administration of a physical or chemical signal (e.g., administration of a compound such as a phorbol ester). Such a protein may be selected from the group consisting of cytosolic protein kinases, protein phosphatases, adapter proteins, cytoskeletal proteins, cytoskeleton associated proteins, GTP-binding proteins, plasma transmembrane proteins, plasma membrane associated proteins, β-arrestin, and visual arrestin (including fragments thereof that specifically bind to an internal structure). Preferably, the protein is a protein kinase C isoform or a fragment thereof that specifically binds to an internal structure, such as a C1 domain fragment or a C2 domain fragment of protein kinase C gamma (or other suitable protein kinase C), where the induction signal is administration of a phorbol ester. In addition, induction of translocation may be induced by stimulation of a receptor, such as a glutamate receptor, beta-adrenergic receptor, or PAF receptor, with a receptor agonist to induce a signaling step which in turn induces translocation. Finally, numerous proteins may be modified to make them translocatable by employing bridging molecules, as discussed above.

As noted above, in one embodiment of the invention the first and second proteins of interest may together comprise members of a specific binding pair. In this embodiment, the invention may further include the step of administering a test compound to the cell prior to the detecting step, wherein the absence of binding of the detectable group to the internal structure indicates that the test compound inhibits the binding of the members of the specific binding pair. Any test compound can be used, including peptides, oligonucleotides, expressed proteins, small organic molecules, known drugs and derivatives thereof, natural or non-natural compounds, etc. Administration of the test compound may be by any suitable means, including direct administration such as by electroporation or lipofection if the compound is not otherwise membrane permeable, or (where the test compound is a protein), by introducing a heterologous nucleic acid that encodes and expresses the test compound into the cell. Such methods are useful for screening libraries of compounds for new compounds which disrupt the binding of a known binding pair.

FIG. 1 is a schematic illustration of an evanescent microscope 10 of the invention, useful for carrying out a quantitative translocation analysis (QTA). A prism 11 is used as the total internal reflection (TIR) member. The prism is a dove prism made of crown glass (part number 01PDE005, Melles Griot, Irvine, Calif.). Excitation light 12 (argon ion laser at 488 nm) for generating the evanescent field is provided by an Enterprise argon-ion laser 13 obtained from Coherent Inc., Moutainview, Calif. A glass cover slip 14 made of crown glass has cells adhered thereto, and is contacted to the dove prism with an intervening coating of oil (Immersionsol N518 from Zeiss, Inc.). The angle of the laser light into the TIR member is adjusted to provide an evanescent field in first and (weakly) second portions of the cells, as explained above. A Zeiss Axioskop microscope stand is used as a stand for a Princeton Instrument CCD 1300-Y 15 (Trenton, N.J.) photon detection system, which is in turn connected to a personal computer programmed with appropriate data collection and analysis software.

Figure 2:
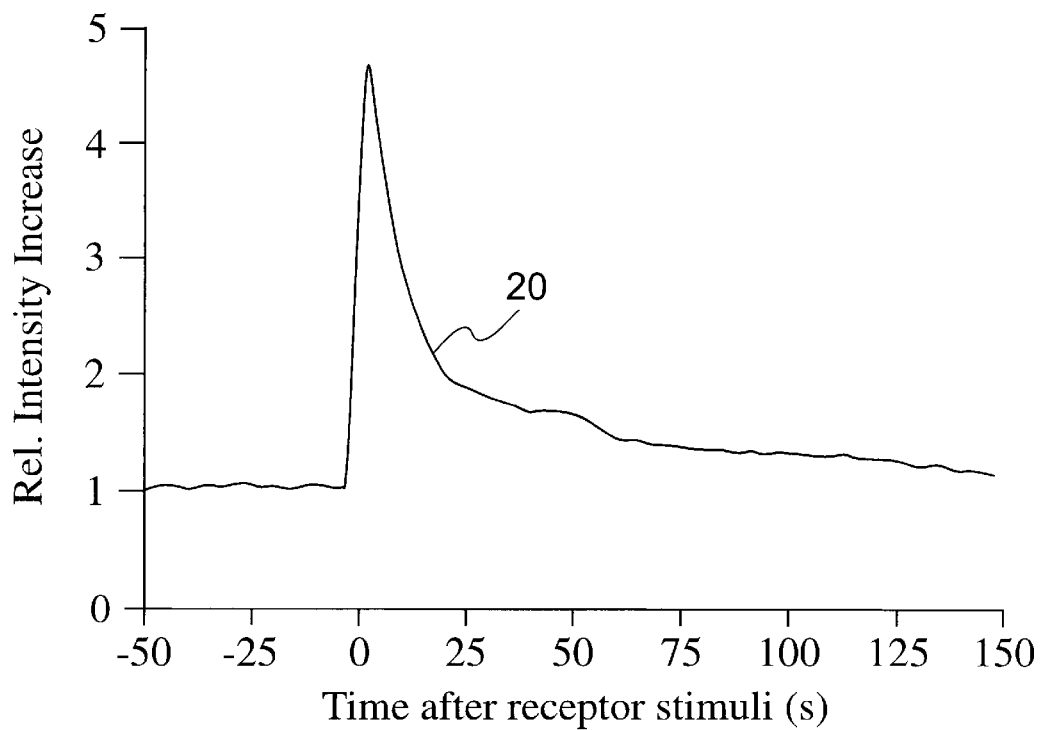
FIG. 2 demonstrates a quantitative translocation analysis carried out with an apparatus of FIG. 1.

FIG. 2 demonstrates a quantitative translocation analysis carried out with an apparatus of FIG. 1. RBL cells expressing C2-GFP were stimulated with PAF. The fluorescence signal average 20 was measured from 6 cells. Each cell had relative signal increases that ranged from 3 to 6 fold.

Figure 3:
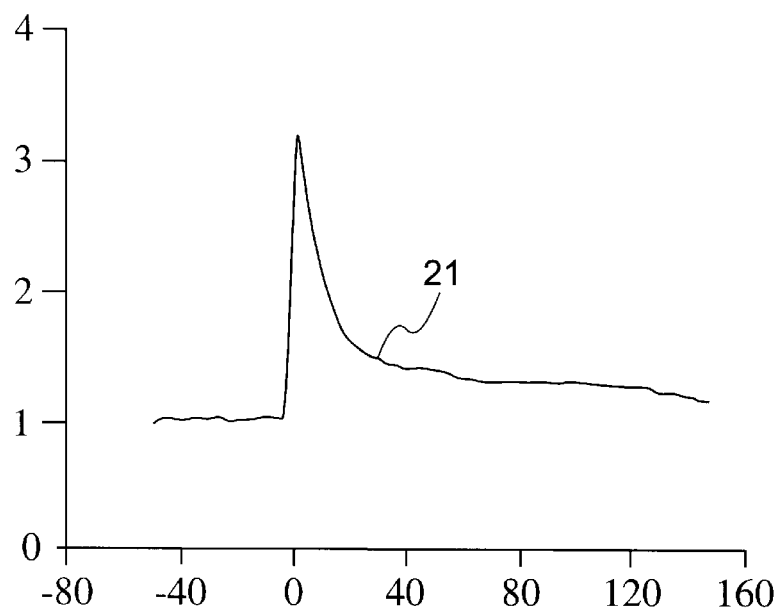
FIG. 3 demonstrates a photomultiplier simulation of a quantitative translocation analysis signal.

FIG. 3 demonstrates a photomultiplier simulation of a quantitative translocation analysis signal, with the same data analyzed as for the single cells in FIG. 2 above. The average relative fluorescence increase 21 for the entire field of view (simulating what a photomultiplier would encounter) is illustrated. The field of view was approximately 0.15 mm in diameter.

Figure 4:
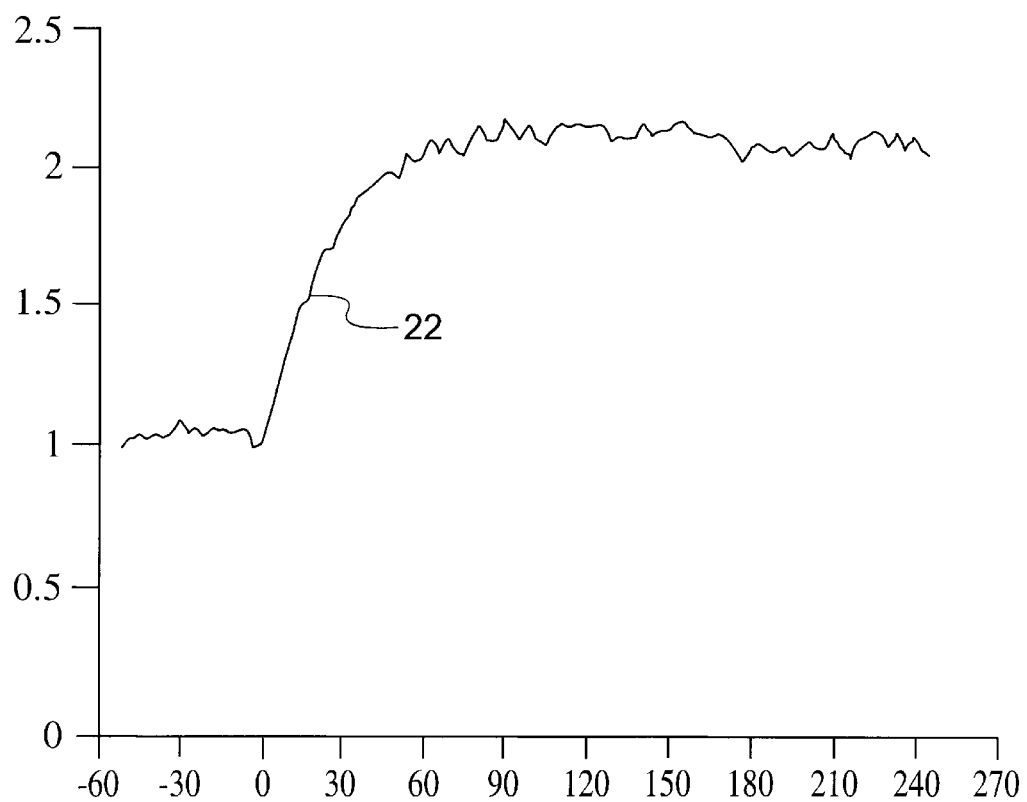
FIG. 4 shows PAF induced plasma membrane translocation of C1-GFP measured by evanescent microscopy with an apparatus of FIG. 1.

FIG. 4 illustrates PAF induced plasma membrane translocation of C1-GFP measured by evanescent microscopy with an apparatus of FIG. 1. The relative increase in fluorescence intensity 22 for an average of six cells is shown at 3 second time-points.

Figure 5:
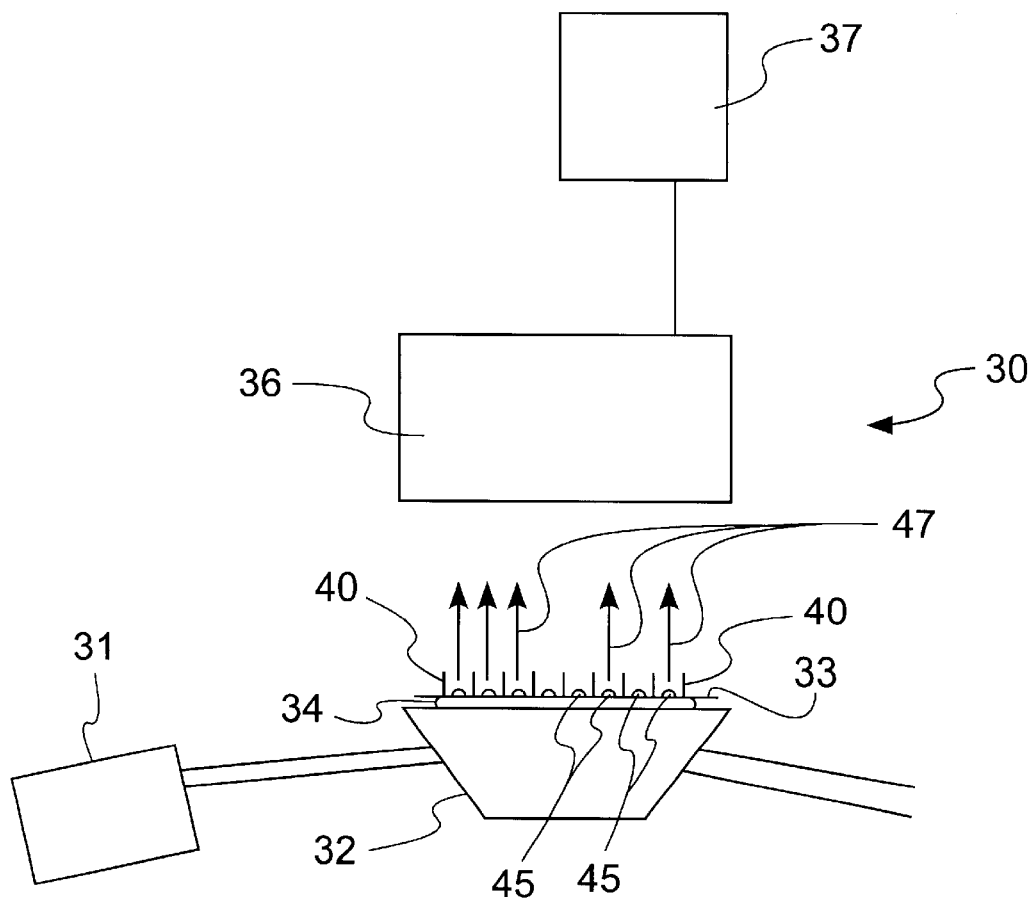
FIG. 5 illustrates an apparatus of the present invention for screening a plurality of cells.

FIG. 5 illustrates an apparatus of the present invention for simultaneously screening a plurality of cells. The apparatus comprises a light source 31, a prism 32, a substrate 33 positioned on top of the prism and optically contacted to the prism by means of an oil 34 with a similar index of refraction to the substrate and the prism, an optical detection system 36 and a computer 37. The light source, prism, and substrate may be the same as the light source, prism and substrate described in Example 1 above. The substrate is divided into segments by a rigid polymer grid 40 that is secured to the substrate by means of an adhesive. Cells 45 are adhered to the substrate in each of the discrete regions, as described above. Excitation light 46 produces an evanescent field in first regions of the cells which in turn generates a light signal 47 from the cells that is detectable or distinguishable by detection system 36 when the fluorescent group is in the first region of the cells. The various components of the system can be used in like manner to that described in U.S. Pat. No. 5,633,724 (the disclosure of which is incorporated by reference herein in its entirety), except that cells are employed in contrast to compounds. The discrete regions on the substrate can be formed by any suitable means, such as by adhering a physical barrier such as a grid to the substrate, simply adhering cells in different regions, forming wells, channels, grooves or other physical barriers in the substrate, etc. The apparatus of FIG. 5 can be used for the simultaneous screening of a plurality of cells, which may be the same or different.

Figure 12:
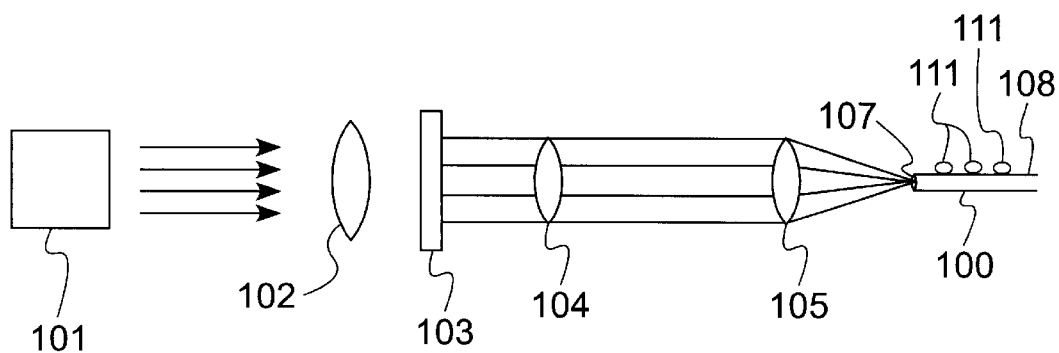
FIGS. 12 and 13 illustrate schematic diagrams representative of the apparatuses of the invention. Although specific embodiments are set forth therein, it should be appreciated that modifications to these embodiments can be made without altering the scope of the invention. For example, lenses of different shapes, dimensions, and geometries can be employed, as well as different lasers.
Figure 13:
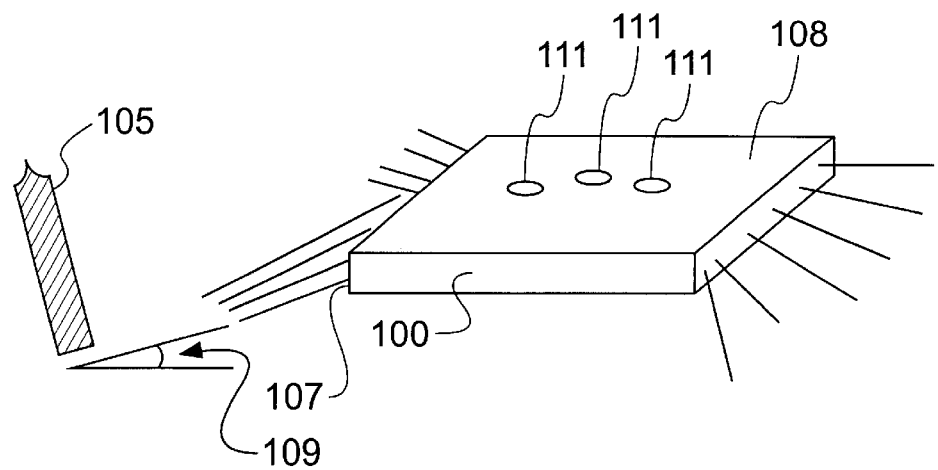

In the embodiment of an apparatus shown in the FIGS. 12 and 13, a coverslip 100 (e.g., a 22 mm×22 mm coverslip) or the like serves as thin unitary total internal reflection member. The apparatus includes an expanded laser 101 (e.g., 442 nm He Cd ; 514 nm Ar), a cylindrical lens 102 (e.g., f=60 mm), a rotating diffuser 103, a collection lens 104 (e.g., f=125 mm) and a focussing lens 105 (e.g., fn 125 mm). The coverslip has a polished edge portion 107 and a top surface portion 109. The laser light is focused onto a 20 mm long line on the diffuser, and the line is projected onto the edge of the coverslip at an angle 109 of about 15 degrees to enable total internal reflection in the covership. A plurality of cells 111 contacted to the surface portion 108 by the plasma membrane of the cells so that emission from proteins of interest therein may be detected as described above. This device utilizes a fluorescent imaging approach based on evanescent wave excitation (also termed total internal reflection fluorescence microscopy, Axelrod, D. (1981) *J. Cell. Biol.* 89, 141–145) to more quantitatively measure plasma membrane translocation processes. Compared to confocal microscopy, evanescent wave imaging significantly increased (i) the signal-to-background when measuring the fraction of plasma membrane translocated protein, (ii) the spatial resolution when measuring the membrane distribution of localized proteins and (iii) the throughput of translocation measurements by enabling measurements of translocation events simultaneously in more than a thousand cells. These studies suggest that evanescent wave excitation of translocating fluorescent proteins and minimal protein domains is a powerful live cell imaging tool to measure signaling and binding events in the context of different signaling pathways and cell types.

EXAMPLE 1

Materials and Methods

Cell Culturing. Rat basophilic leukemia 2H3 (RBL) cells were grown and plated as described by Oancea, et al. ((1997) *J. Cell Biol.* 140, 485–498) and Oancea, E. & Meyer, T. ((1998) *Cell* 95, 307–318). RBL cells with stably transfected PAF receptors were obtained from the laboratory of Ralph Snyderman (Duke University). Hippocampal astrocytes were used from mixed neuron/glia cultures prepared as described by Teruel, et al. ((1999) *J. Neuroscience Methods* 93:37–48). The cultures were maintained at 37° C. in a 95% air, 5% $CO_2$ humidified incubator, and used 7 to 14 days after plating.

Cloning of GFP-Fusion Constructs and Electroporation. The cloning of the cDNA encoding the C-terminal palmitoylation/myristoylation sequence from Lyn was described by Teruel, et al. ((1999) *J. Neuroscience Methods* 93:37–48)) and the synthesis of in vitro transcribed RNA of CaMKIIα, C1-CaMKIIα and C1-CaMKIIβ were described by Yokoe, H. and Meyer, T. ((1996) *Nat. Biotechnol.* 14, 1252–1256). The cDNAs for the full-length PKCγ and the $C1_2$ domain of PKCδ were cloned into the EGFP-N2 vector (Clontech). The C2 domain of PKCγ with an N-terminal EGFP was cloned into pcDNA3 vector (Invitrogen). The PH-domain of Akt was cloned into the EGFP-C1 vector (Clontech). The cDNA or RNA constructs were transfected by a microporation device for adherent cells (Teruel, M. N. & Meyer, T. (1997) *Biophys. J.* 73, 1785–96; Teruel, et al. (1999) *J. Neuroscience Methods* 93:37–48).

Evanescent Wave Excitation and Fluorescence Microscopy (also termed Total Internal Reflection Fluorescence Microscopy or TIRFM). Evanescent wave fluorescent excitation for studies of cells was introduced by Axelrod ((1981) *J. Cell. Biol.* 89, 141–145), and different versions of such microscopes have been made since then (Lang et al. (1997) *Neuron* 18, 857–863; Thompson, N. L. & Lagerholm, B. C. (1997) *Curr. Opin. Biotechnol.* 8, 58–64). In this method, the reflected light produces an exponentially decaying light field above the glass-water interface with a space constant given by the angle of the incident light source. For glass coverslips, total internal reflection occurs for angles above 61° [$\theta_{l,c}$=arcsin($n_2/n_1$), calculated for a refractive index $n_1$=1.52 for glass and $n_2$=1.33 for water]. For measurements of receptor-triggered translocation, we found that total internal reflection angles of 70° are a suitable compromise between having a sufficiently deep penetration depth (which decreases with increasing angles) and generating unwanted stray light due to scattering objects in the light path (which increases with the angle). The space constant of the exponential decay I(z)=I(0)exp(−z/d) at a given angle can be calculated as described by Axelrod ((1981) *J. Cell. Biol.* 89, 141–145).

$$d=\lambda_o/[4\pi(n_1^2*\sin^2(\theta_i)-n_2^2))^{1/2}]=75 \text{ nm; with } \lambda_o=488 \text{ nm and } \theta_I=70° \tag{1}$$

An evanescent wave microscope configuration optimized for long term live cell imaging with minimal focus drift while having free access to the bath solution for buffer exchange and cell manipulation was designed. The system was built around a Zeiss Axioskop 2 microscope with a focusable water immersion objective. The laser excitation beam entered from below the coverslip through a spatially fixed dove prism (Edmund Scientific). Cells were illuminated by coupling the laser into the coverslip through a 200 μm thin microscope immersion oil layer between the coverslip and the prism. Cells were grown on 25 mm square Type II coverslips in a chamber enclosed by a Teflon ring (3 mm wide and 3 mm high) that contained the extracellular buffer solution. In order to be able to look at different regions on the coverslip, the coverslip itself—but not the fixed prism and objective—was directly mounted on a motor controlled x-y stage.

The cells expressing GFP fusion proteins were excited using a 488 nm laser line (Coherent, typically 10–100 mW) and a 500 nm long pass filter for emission (Chroma Inc.).

A self-built rotating diffuser was used to homogenize the laser light. The diffuser is a device to make the laser light more homogeneous for the imaging. It consists of a conventional motor that has a shaft with a light shaping diffuser mounted at the end of it (we have tried 0.5 and 1 degree diffusers from Physics Optics Corporation, and both work very well). By rapidly rotating the diffuser the laser light becomes more homogeneous than by just leaving the laser on the same spot on the diffuser.

An 85 mm focal distance lens was used to image the scrambled light source onto the prism. The light emitted by the fluorescent proteins was collected by a cooled CCD videocamera (Micromax, 5 MHz, Princeton Instrument). Time series of images were recorded using Metamorph software (Universal Imaging). Experiments were carried out at room temperature (~25° C.).

Construction of an Evanescent wave Single Cell Array Macroscope (E-SCAM). A wide-field microscope (macroscope) was designed in similar fashion to the higher magnification system described above. Two Rodenstock 100 mm Heligon lenses were mounted below the coverslip in opposite directions to obtain a combined objective and ocular with 1:1 magnification. The second lens projected the sample image onto a 5 MHz Micromax camera made commercially available from Roper Scientific of Trenton, N.J. This lens combination has high spatial and chromatic accuracy as well as a numerical aperture of NA~0.3 (F/1.6).

An important feature of this E-SCAM design is the coupling of the scrambled laser light directly into the polished edge of a coverslip (Type II, 22×22 mm) using a cylindrical lens. The polished angle was set at 20 degrees from vertical to generate a light guide within the coverslip. The coverslip was mounted on a z-direction adjustable stage and a teflon ring was used for containing the solution in the cell chamber.

For coupling, we used two Rodenstock cylindrical lenses, the top lens (closer to the sample) images the cell sample to infinity. The second lens was mounted in the opposite orientation to focus the image back onto the CCD camera. The distance between the two lenses was 120 millimeters, which allowed a dichroic mirror to be inserted for an alternative epifluorescence excitation of the cell sample. This space also contains the barrier filters for the emitted light.

An important consideration is the grease or other adhesive used to fix the cell chamber (or the wells) to the coverslip. The grease should have a refractive index >1.38 or better >1.4 in order for the coupling to work most effectively. The angle of the incident light has to be adjusted to ensure total internal reflection within the coverslip. We have tested this empirically by maximizing the light exiting the coverslip while grease or adhesive is present on a calibration coverslip. We are currently using a Dow Corning High Vacuum Silicon grease for attaching the buffer solution-containing cell chamber to the coverslip.

EXAMPLE 2

Results

Figure 6:
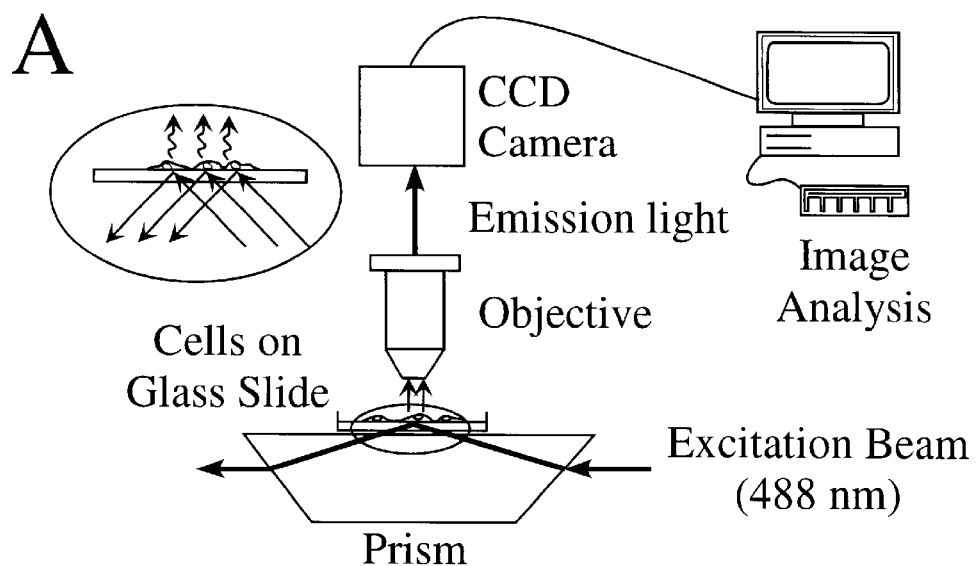
FIG. 6. Evanescent wave excitation of fluorescent cytosolic and membrane proteins in adherent cells. (A) Schematic view of the microscope setup (see Materials and Methods section for description). (B) Fluorescent images of RBL cells that express cytosolic GFP (left; representative of 6 experiments) or plasma membrane targeted GFP (right, n=3). A myristoylation/palmitoylation sequence was fused to the N-terminal end of GFP for membrane targeting. While expressed at a similar level, the membrane targeted GFP exhibited a 3 to 10-fold higher fluorescence intensity than the cytosolic GFP (Bar=10 μm).
Figure 6:
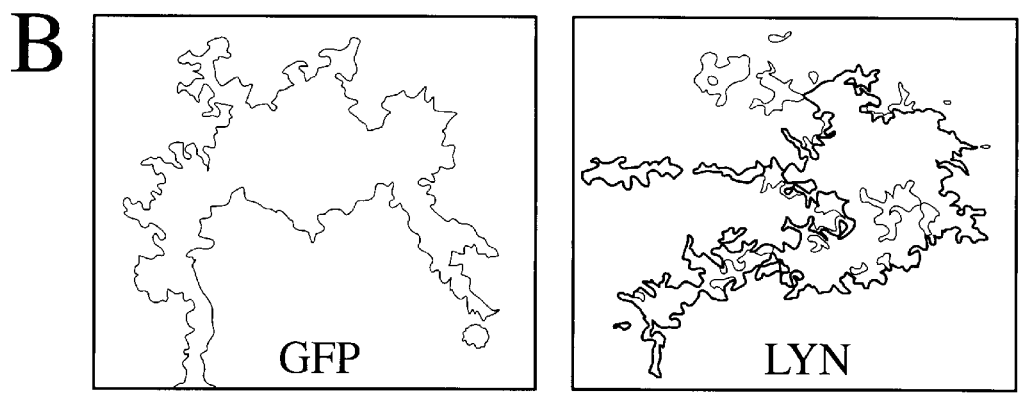

Selective Imaging of Fluorescent Proteins at the Plasma Membrane by Evanescent Wave Excitation. An evanescent wave microscope (also termed total internal reflection fluorescence microscopy or TIRFM) was built to excite and monitor fluorescence signals from the adherent plasma membrane of living cells by selectively illuminating an ~75 nm deep region above the glass surface (see Material and Methods for design features). The microscope was optimized for having access to cells while performing long term imaging experiments without a focus drift. A schematic representation of the microscope setup is shown in FIG. 6A.

Fluorescent images were recorded from RBL-cells that had similar levels of expressed cytosolic or plasma membrane localized GFP constructs. The targeting of GFP to the plasma membrane utilized a fusion of the 12 amino acid palmitoylation/myristoylation plasma membrane targeting sequence from Lyn to the N-terminus of GFP (Teruel, et al. (1999) *J. Neuroscience Methods* 93: 37–48). The fluorescence intensity of cells with expressed cytosolic GFP (FIG. 6B) was typically 3 to 10-fold lower than the intensity of cells with expressed plasma membrane targeted GFP (FIG. 6C). When compared to confocal microscopy images of the same cells, evanescent wave imaging of membrane localized GFP showed a better fine resolution of the organization of the adherent plasma membrane, suggesting that the much thinner section of excitation in evanescent wave imaging (75 nm instead of several hundred nm in confocal) markedly reduced blurring.

Figure 7:
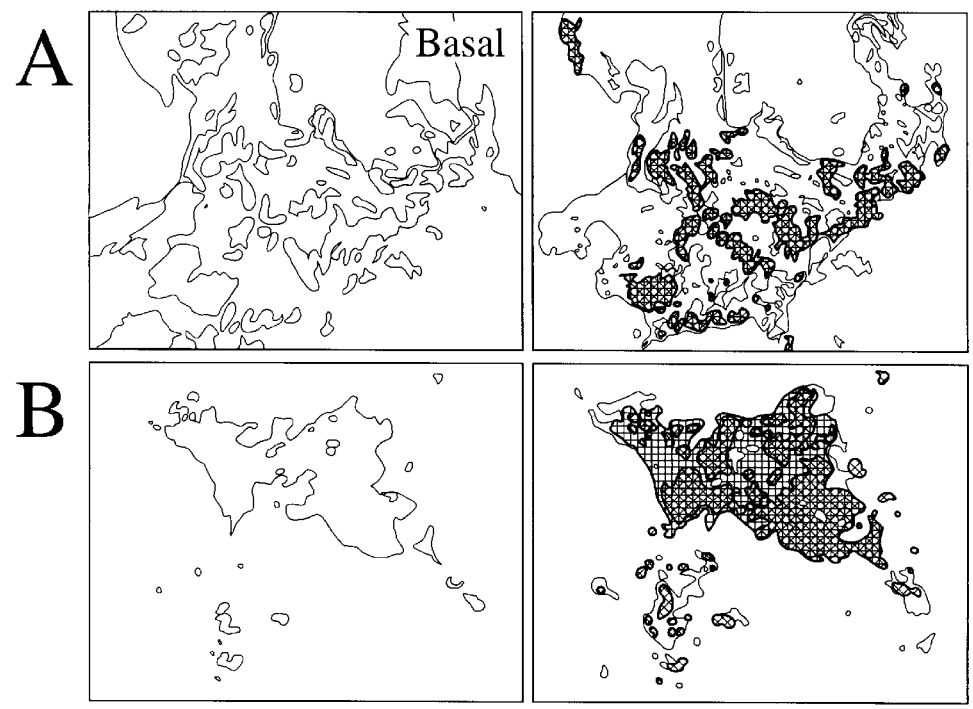
FIG. 7. Plasma membrane translocation of PKCγ measured in hippocampal astrocytes by evanescent wave excitation. (A) Time series of fluorescent images of cultured hippocampal astrocytes expressing PKCγ-GFP stimulated with glutamate (100 μM; n=47). A marked increase in fluorescence intensity was observed. (B) The same experiment as in (A) but with calcium ionophore added (2 μM ionomycin; n=8). (Bars=10 μm in (A) and (B)). (C) Time course of PKCγ-GFP translocation measured as a fractional increase in fluorescence intensity and triggered by glutamate addition (100 μM, left) to a single astrocyte (left panel; n=47). (D) Similar periodic intensity changes in an RBL stably expressing PAF receptors following the addition of 100 nM PAF. Ionomycin was added at the end of each experiment (2 μM).

Analysis of Receptor Triggered Translocation of PKCγ-GFP in Thin Cells. The dynamics of receptor-induced plasma membrane translocation of PKCγ-GFP (Sakai, et al. (1997) *J. Cell Biol.* 139, 1465–1476; Oancea, et al. (1997) *J. Cell Biol.* 140, 485–498) was investigated in hippocampal astrocytes. The flat morphology of these cells defeated our earlier attempts to use a confocal microscopy approach for such measurements. Strikingly, glutamate stimulation led to a marked increase in fluorescence intensity that could be clearly resolved by fluorescence imaging (FIG. 7A). Addition of the calcium ionophore ionomycin (FIG. 7B) also triggered a similar increase in fluorescence intensity, confirming that calcium signals are sufficient for translocation of PKCγ. As a control that the intensity increase was a result of translocation, ionomycin and phorbol ester were added to cells expressing the plasma membrane localized GFP construct shown in FIG. 6B, and no significant change in fluorescence intensity could be observed. The changes in fluorescence intensity could be followed in a series of several hundred images. FIG. 7C shows that the typical glutamate-induced translocation events in astrocytes showed rapid oscillations, similar to the oscillating calcium signals that have been observed previously (Yagodin, et al. (1994) *J. Neurobiol.* 25, 265–280). Similar receptor-triggered fluorescence intensity oscillations could be observed in RBL cells (FIG. 7D) and 3T3 fibroblasts (data not shown).

Minimal Protein Domains as Translocating Biosensors for Localized Signaling Events. PKCγ has at least three distinct plasma membrane binding interactions, which are mediated by two C1 domains and a C2-domain (14,33–35). This makes the translocation of the full-length PKC protein a complex signaling event that reflects both calcium and diacylglycerol signals as well as potential PKC-adaptor interactions (Mochly-Rosen, D. (1995) *Science* 268, 247–251). Thus, owing to their better defined molecular specificity, minimal protein domains are often better suited as biosensors to dissect the spatial and temporal dynamics of a specific signaling process.

Figure 8:
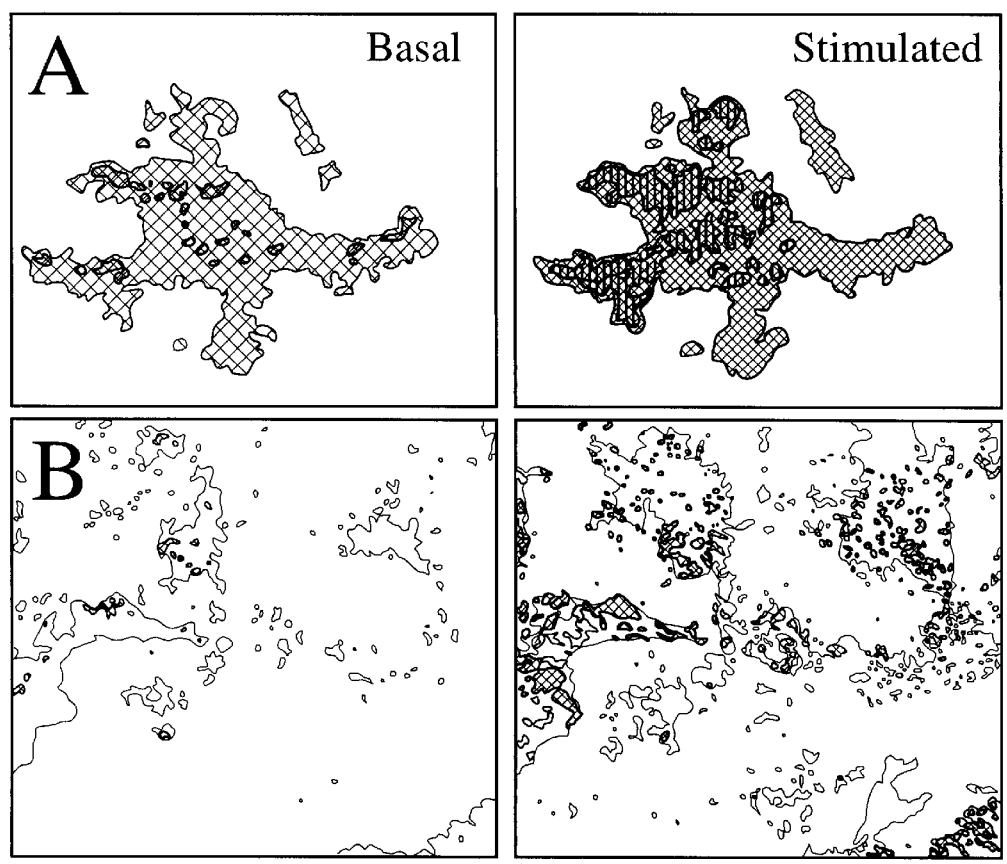
FIG. 8. Measurement of the plasma membrane translocation of GFP-tagged minimal protein domains. (A) Translocation of GFP-PH domain of Akt (or also termed PKB) triggered by addition of PAF (1 μM) to RBL cells (n=2). Cells were kept for 10 hours in serum-free medium before stimulation. (B) Translocation of $C1_2$-GFP domain from PKCδ triggered by addition of diacylglycerol (DiC8, 0.5 mM) to cultured hippocampal astrocytes (n=12). (Bars=10 μm).
Figure 9:
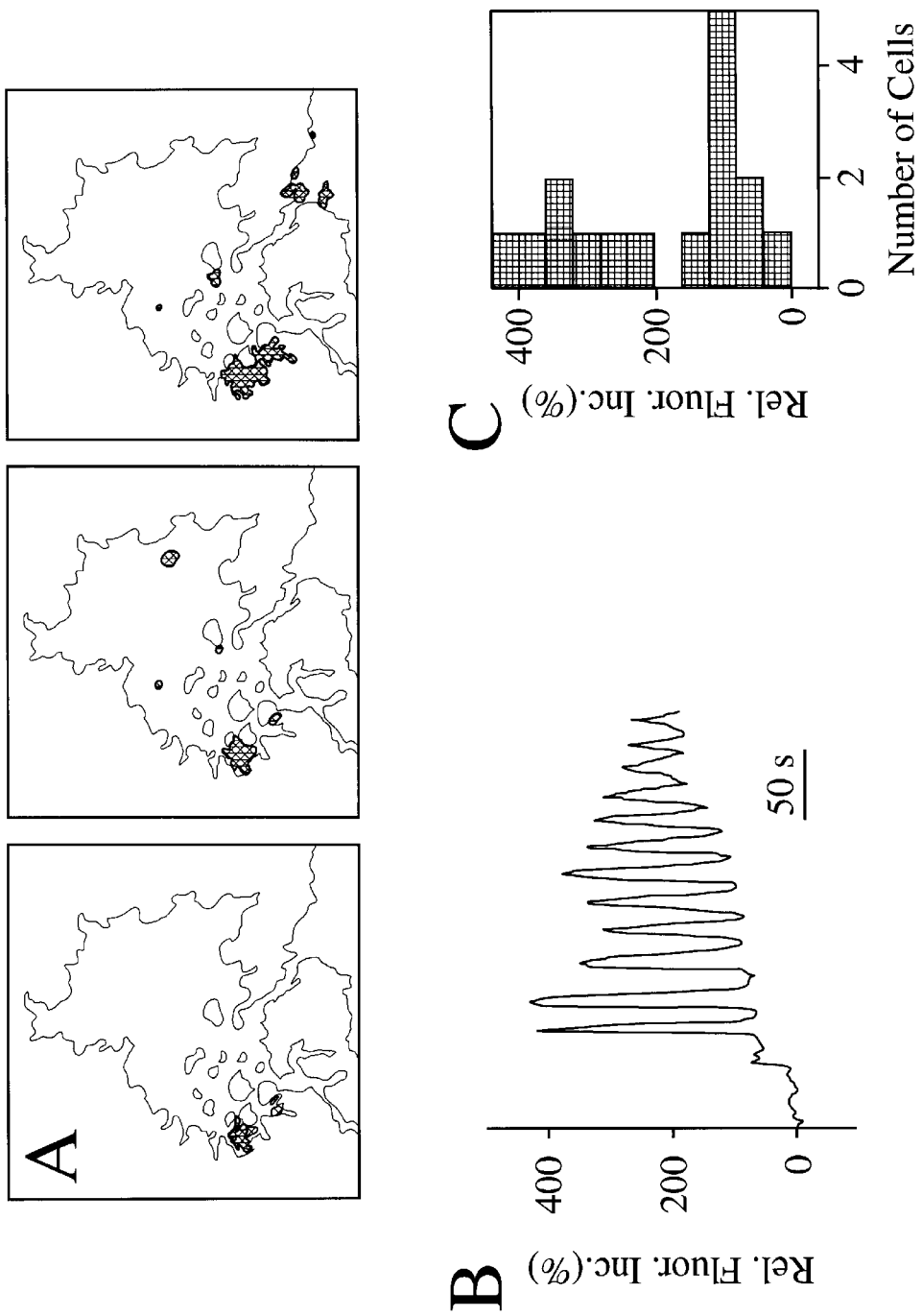
FIG. 9. Local translocation and cell-to-cell variability of translocation events. (A) Stimulation of astrocytes with low concentrations of glutamate triggered local transient translocation events of expressed GFP-C2 (PKCγ) domain (n=2). Since this C2 domain has been shown to bind negatively charged lipids in the presence of calcium, these local translocation events likely reflect local increases in calcium concentration. Bar=10 μm. (B and C) Statistical analysis of GFP-C2 domain translocation in PAF-receptor expressing RBL-cells stimulated with PAF (100 nM). (B) Typical time course of the stimulus-induced repetitive translocation events in an individual cell. (C) Analysis of the relative fluorescence increase of C2 domain translocation of 16 cells in the field of view. The histogram shows the number of cells with a given relative fluorescence increase, $R=(I_1-I_0)/(I_0-BG)$, where $I_0$ represents the basal fluorescence intensity and $I_1$ is the intensity after the maximal translocation of the fluorescent construct. BG is the background value.

Evanescent wave imaging was used to measure the translocation of such minimal GFP-conjugated protein domains. For example, FIG. 8A shows a measurement of the PAF receptor stimulated production of 3' phosphorylated phosphatidylinositol lipids measured by the translocation of the GFP-tagged PH domain of Akt (Kontos, et al. (1998) *Mol. Cell Biol.* 18: 4131–4140; Meili, et al. (1999) *EMBO J.* 18, 2092–2105; Watton, S. J. & Downward, J. (1999) *Curr. Biol.* 9, 433–436). In FIG. 8B, a tandem C1 domain from PKCδ is used as a diacylglycerol reporter in astrocytes. In many cases, the translocation of minimal protein domains was markedly local within the plasma membrane, a finding which was not previously apparent from confocal imaging studies. FIG. 9A shows a series of evanescent wave images in which such localized translocation events can be observed in glutamate stimulated astrocytes that express the GFP-tagged C2 domain from PKCγ. Localized translocation of C2-domains can be explained by the earlier observations that cell-wide calcium signals are generated from localized calcium release events (Yagodin, et al. (1994) *J. Neurobiol.* 25, 265–280; Bootman, et al. (1997) *Cell* 91, 367–373; Home, J. H. & Meyer, T. (1997) *Science* 276, 1690–1693; Parker, I. & Yao, Y. (1996) *J. Physiol. (Lond)* 491, 663–668). The finding of local translocation events suggests that local second messenger signals have a functional relevance in localized target activation.

Although there was a significant cell-to-cell variability in single cell measurements of different signaling events, a significant fraction of cells typically respond to a receptor stimulus. An analysis of the time-course of translocation of the C2-GFP in PAF stimulated RBL cells (FIG. 9B) shows that most cells responded with a relative peak increases in plasma membrane fluorescence signals between 100% and 200% (FIG. 9C).

Measuring Protein-Protein Binding Interactions with High Signal-to-Background by Evanescent Wave Excitation. Protein-protein binding interactions have been measured previously by using a dual protein fusion strategy in which a protein Y was conjugated with an inducible plasma membrane translocation domain and a protein X with a GFP-tag (FIG. 5A, ref. 40). By inducing plasma membrane translocation of the non-fluorescent protein Y, the increase in plasma membrane fluorescence from the fluorescent protein X becomes a measure for the fraction of protein X that is bound to protein Y (since it is carried along with protein Y to the plasma membrane). A main limitation of this binding assay was that the data had to be extracted by performing a confocal image analysis of the plasma membrane versus the cytosolic distribution of the GFP-tagged protein X.

Figure 10:
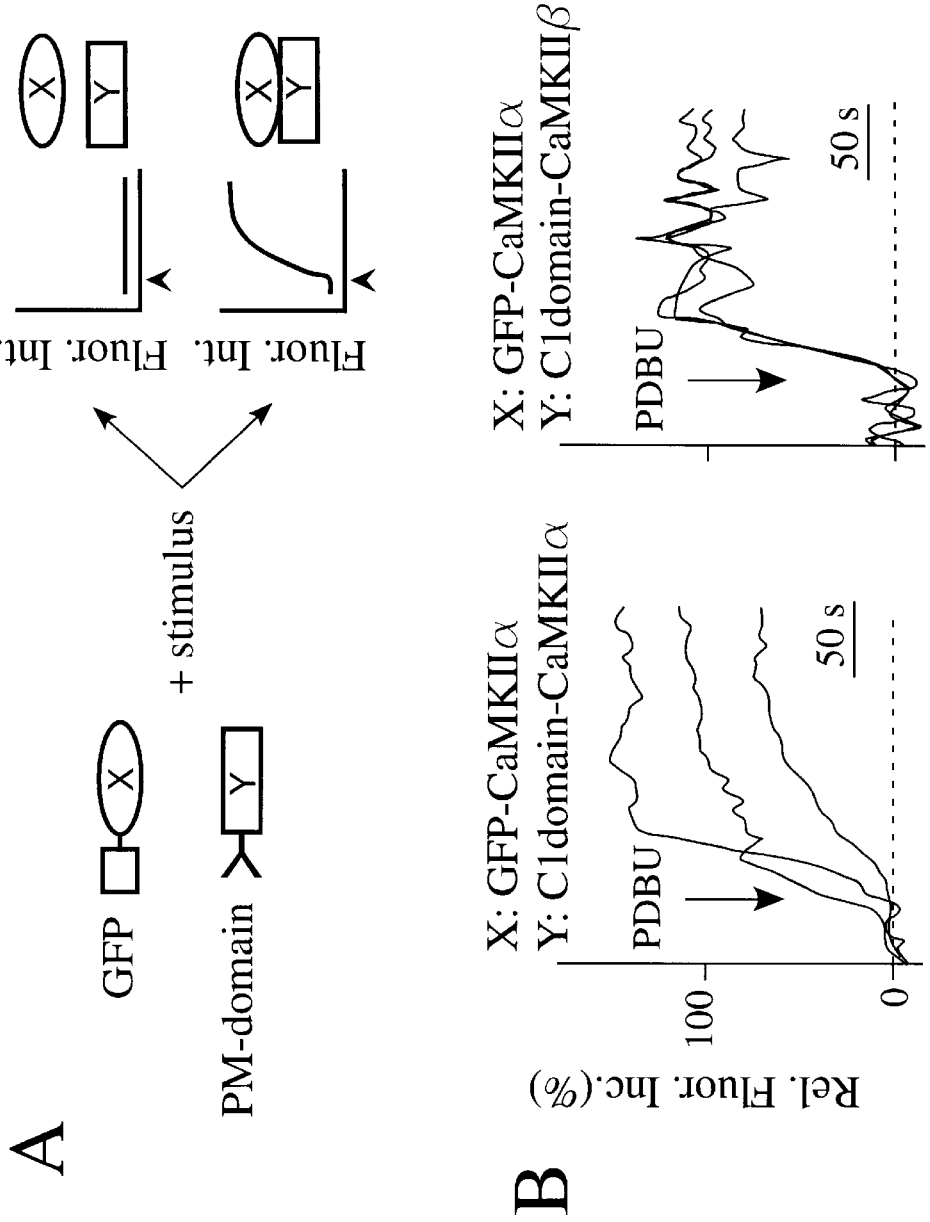
FIG. 10. Measuring protein-protein binding interactions of cytosolic proteins using an evanescent wave excitation. (A) Schematic representation of the in vivo binding assay. Binding between Proteins X and Y can be measured by conjugating Protein X with GFP and Protein Y with an inducible plasma membrane targeting domain. (B) Demonstration that evanescent wave excitation can be used to measure binding interactions between two CaMKII isoforms. The C1A-domain from PKCγ was used as an inducible translocation domain. (Left) Phorbol ester addition (PDBu, 1 μM) to RBL-cells that express C1A-CaMKIIα and GFP-CaMKIIα triggered a marked increase in plasma membrane fluorescence, consistent with the previous findings that CaMKIIα forms multimers (n=3). (Right) Phorbol ester addition to RBL-cells that express C1A-CaMKIIβ and GFP-CAMKIIα lead to a similar fluorescence increase, demonstrating that CaMKIIα and CaMKIIβ bind to each other in the cytosol (n=2). Typical translocation traces are shown.

Evanescent wave excitation was now used in combination with the same assay. The C1A domain from PKCγ was employed as a phorbol ester inducible plasma membrane translocation domain and the same binding partners CaMKIIα and CaMKIIβ were investigated that were used in the previous confocal imaging study. RNA transfection was used for quantitative expression of the two constructs (Teruel, et al. (1999) *J. Neuroscience Methods* 93: 37–48). Addition of phorbol ester, which induced the translocation of the C1A domain conjugated CaMKIIα, triggered a rapid fluorescence increase resulting from the plasma membrane translocation of coexpressed GFP-tagged CaMKIIα (FIG. 10B), suggesting that CaMKIIα forms homo-oligomers. For the binding between the α and β isoforms, CaMKIIβ was conjugated with the C1A domain and co-expressed with GFP-tagged CaMKIIα. Again, the phorbolester induced increase in the evanescent wave excited fluorescence signal demonstrates that the two isoforms bind to each other (FIG. 10C). This shows that cytosolic protein-protein binding interactions can be monitored by evanescent wave excitation in intact cells.

Simultaneous Measurements of Translocation Events in Thousands of Cells Using an Evanescent Wave Macroscope. The studies above were performed with high magnification in order to resolve spatial differences in the local distribution of GFP tagged proteins. This limits each experiment to the analysis of a few cells. In many cases, several days worth of experiments are needed to extract statistically significant information from a specific cellular response. A significant advantage of evanescent wave imaging is that translocation measurements are reduced to an increase in local fluorescence intensity and do not require subcellular image analysis as is needed in confocal microscopy. The image magnification can therefore be significantly reduced so that translocation signals can be measured simultaneously from large number of cells.

Figure 11:
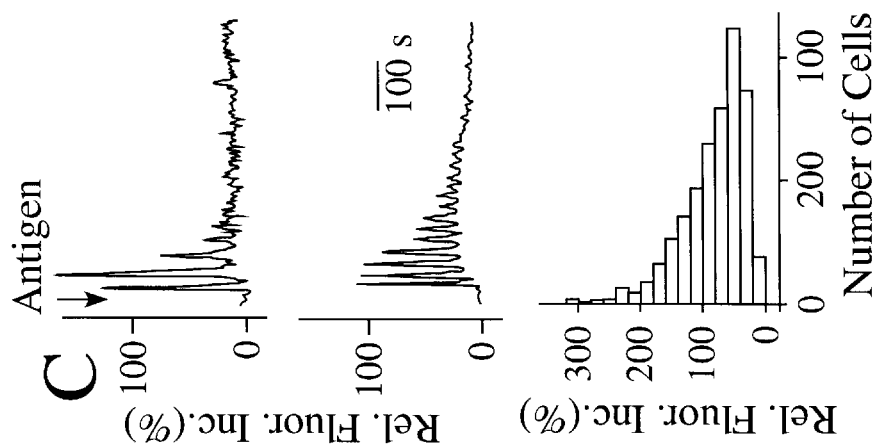
FIG. 11. E-SCAM measurement of plasma membrane translocation events in more than a thousand cells. (A) Schematic view of the Evanescent wave Single Cell Array Macroscope (E-SCAM) in which the excitation light is directly coupled into the coverslip. (B) Low magnification images of RBL, cells expressing PKCγ-YFP before (left) and after stimulation with calcium ionophore (right). The insert shows a more detailed view of a subregion of the image. (Bar=1 mm). (C and D) Statistical analysis of receptor-triggered fluorescence intensity changes measured in RBL-cells expressing PKCγ-YFP after stimulation by cross-linking of their FcεRI receptors with the antigen DNP-BSA. (C) Typical time courses. (D) Histogram of the maximum amplitude of fluorescence intensity changes that was measured in each of more than 1000 cells visible in the field of view.
Figure 11:
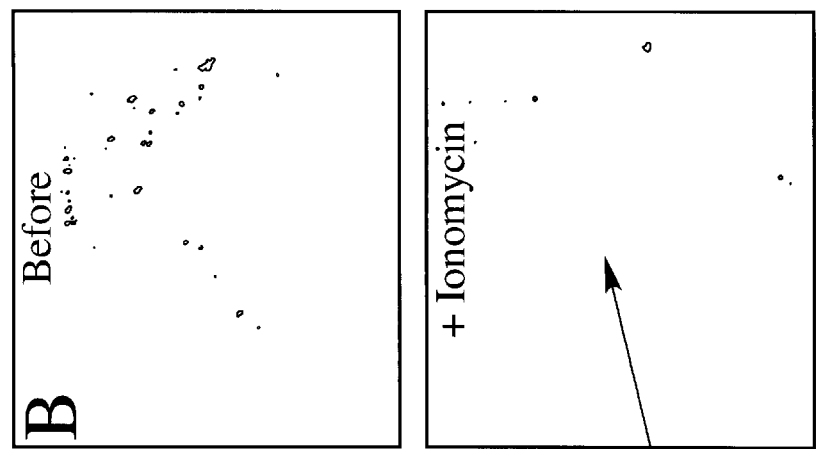
Figure 11:
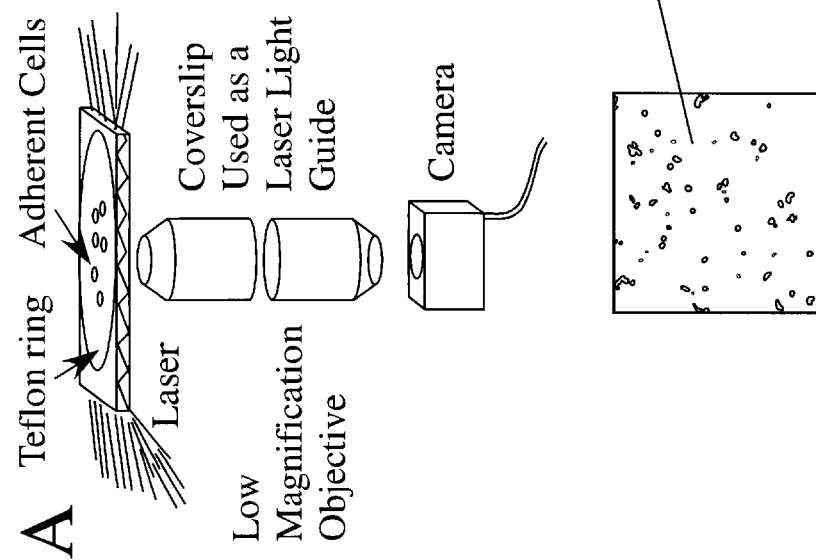

A light sensitive macroscope with a 1× magnification that projects the coverslip surface onto a CCD camera was built. A new laser coupling strategy was developed, in which a laser beam was focused by a cylindrical lens directly into the polished and angled edge of a coverslip to generate a "coverslip light guide". The laser light was then reflected numerous times within the coverslip, generating an evanescent light field in a large surface area that could be imaged without any need for a prism or oil coupling. The lens system and the CCD camera could then be mounted below the coverslip (FIG. 11A). Because of the large surface area that can be imaged in this system it was termed an Evanescent wave Single Cell Array Macroscope or E-SCAM.

The consistency of cellular responses was tested by monitoring the ionomycin-induced plasma membrane translocation of PKCγ. FIG. 11B shows an image of transfected RBL cells before and after ionomycin addition. A marked increase in the fluorescence intensity can be seen for all individual spots, each representing the fluorescence from an individual cell. The inset shows a small subregion at higher magnification. The same type of translocation events could also be observed when RBL cells were stimulated by cross-linking FcεRI surface antigen receptors using BSA-DNP (Oancea, E. & Meyer, T. (1998) *Cell* 95, 307–318). The time-courses of the plasma membrane translocation of PKCγ were then analyzed simultaneously for more than a thousand cells. FIG. 11C shows typical time-courses of such translocation events. While ionomycin-induced translocation had a 100% cell compliance with a distribution of the induced fluorescence intensity increase between 100% and 200% of the baseline fluorescence signals (data not shown), the compliance was slightly lower and the amplitude smaller for the translocation triggered by receptor stimuli (FIG. 11D). Together, this shows that the evanescent wave excitation method is a suitable quantitative tool for monitoring signaling events simultaneously in a large number of cells, obtaining statistically significant single cell signaling data in a single experiment.

These studies show that evanescent wave excitation can be used for quantitative measurements of plasma membrane translocation events with high signal-to-background and with marked spatial resolution. For practical consideration, the typical z-resolution (vertical) in evanescent wave microscopy is between 0.05 to 0.1 $\mu$m while it is between 0.4 to 1 $\mu$m for fluorescence images of GFP-constructs using confocal microscopy. The narrow z-resolution in evanescent wave excitation improves the selective excitation of fluorescent proteins at the surface plasma membrane compared to fluorescent proteins in the cytosol, and thereby increases the signal for translocation measurements up to 10-fold. Furthermore, the better z-resolution in evanescent wave imaging minimizes collection of light emitted from below and above the image plane and thereby improves the spatial resolution in the x-y directions compared to that of confocal microscopy. Finally, for GFP-tagged proteins that exchange between sites at the surface plasma membrane and other parts of the cell, evanescent wave imaging significantly reduces photobleaching when compared to conventional imaging methods.

An important consideration in using signaling proteins or domains conjugated with GFP is that the presence of the biosensor can alter some of the signaling responses of the native signal transduction machinery. For example, we found clear evidence for such an inhibition with fluorescently tagged SH2-domains (Stauffer, T. & Meyer, T. (1997) *J. Cell Biol.* 139, 1447–1454). Although this has not been stringently tested, biosensors such as C1, C2 and PH domains that bind lipid second messengers and membranes are likely to require significantly higher expressed concentrations to exhibit inhibitory effects. On the other hand, GFP-labeled signaling enzymes are likely to function as upregulators of a particular signaling step when expressed at higher levels than the native protein. By expressing catalytically inactive mutant constructs, and by measuring responses at different concentrations of the expressed constructs, it is useful to assess the magnitude of such perturbations in a specific cell type.

A second important consideration in evanescent wave translocation studies is that plasma membrane signaling processes in the surface contact area can be different from those in the non-adherent side. Since evanescent wave imaging only excites fluorescently labeled proteins at the plasma membrane near the surface, some signaling events may not be observed. Ligand access to receptors at the bottom of the cell might be a problem in some cell systems, although many cells are expected to adhere to surfaces with sufficient space for small peptides and other compounds to penetrate. These considerations suggest that a particular translocation process should also be investigated using confocal or deconvolution imaging.

A notable practical difficulty in evanescent wave studies of translocation processes is the exponential profile of the excitation field, which can lead to changes in fluorescence intensity caused by cell movement or cell spreading. Control experiments using plasma membrane targeted GFP (FIG. 6) or dual fluorescence imaging with such marker proteins can be used to either identify or correct for such problems.

These studies suggest that evanescent wave imaging of translocation events has several applications for measuring signal transduction processes as they occur in a living cell. Instead of having only a fluorescent calcium readout, a number of diverse signaling processes can now be measured. Such assays will be valuable for studies of signaling feedback and cross-talk processes for different receptor-stimuli and cell types. It will be interesting to determine whether or not limited sets of distinct "signaling states" can be defined in cells after stimulation with single or multiple receptor inputs.

These studies also suggest that the E-SCAM technology will be useful for medium throughput screening applications. Instead of the relatively complex image analysis needed in confocal microscopy studies of translocation events, the translocation in evanescent wave imaging is reduced to a simple change in fluorescence intensity. Given the initial results, it can be estimated that the E-SCAM method can be used to monitor signaling processes in each of more than $10^6$ individual cells. The same type of approach can then also be used in combination with the inducible plasma membrane translocation scheme to measure protein-protein interactions in a large cell number.

In summary, these studies suggest that evanescent wave excitation is a powerful tool in signal transduction for measuring plasma membrane recruitment and dissociation processes. It can be used to study the regulation of signaling gradients and the formation of localized signaling complexes, as well as to understand cross-talk and feedback processes in more complex signaling systems and signal transduction networks. The use of evanescent wave excitation to measure responses from a large number of individual cells suggests that screening applications become feasible for identifying pharmacological agents or expressed protein constructs that enhance or reduce particular signaling events or alter protein-protein binding interactions.

EXAMPLE 3

Screens

Screen 1: Identification of Chemical Libraries, Drug Collections, Peptides, Antisense and Other Compounds that Interfere with Particular Signaling Events. Many signal transduction events result in the translocation of proteins between two cell portions of which one portion is near the plasma membrane. Any such signaling process that leads to such a translocation event can be screened using the evanescent wave method (i.e. calcium (C2-domain), diacylglycerol signals (C1-domains), tyrosine phosphorylation (SH2-domains), phosphatidylinositol polyphosphate signals (different PH-domains), phosphorylation of seven-transmembrane receptors (beta-arrestin). Establishment of cell lines that express the respective translocatable fluorescently conjugated signaling protein or protein domain is recommended.

Useful also as secondary screen of compounds that were identified by in vitro binding assays and which may or may not function as inhibitors in the cellular environment.

Screen 2: Screen for Supressors or Enhancers of Known Signaling Pathways. Screening cDNA libraries for expressed proteins that either suppress or enhance the signal transduction event monitored by the evanescent wave translocation assay.

Screen 3: Screen for Mutant Cells that Show Suppressed or Enhanced Signal Transduction Events. This application includes the screening of randomly mutated cells that show different signaling responses and the subsequent identification of the mutated gene.

Screen 4: Identification of Ligands of Orphan Receptors. Many G-protein coupled, tyrosine kinase and other receptors have unknown ligands. A large set of such ligands or drugs that may bind to the orphan receptor can be identified with this method.

Using a translocatable fluorescent protein downstream of the receptor such as C1, C2, PH-domains or β-arrestin to monitor evanescent wave intensity changes.

Screen 5: Identification of Novel Binding Partners of a Known Protein. Binding interaction between the known protein X and a large number of unknown proteins Y are screened. Protein X is made as a conjugate with a fluorescent group or fluorescent protein while a library of the proteins Y is made that are each coupled to a protein or protein domain that can translocate between the two cell portions in response to addition of a drug, receptor stimuli or other procedure. A cell line is then made using the fluorescent protein X. The library of proteins Y with conjugated translocatable groups is then transfected into these fluorescent cell lines using pooling of the library or random transfection. Binding partners are then identified that show a drug or stimulus induced change in fluorescence intensity. Fluorescene intensities from individual cells or from segments of the evanescent wave apparatus surface are recorded. Either single cells are selected for analysis or segments of cells when pool assays are used.

The inverse screen is also possible with a library of proteins that are each coupled to a fluorescently labeled protein and a single known protein that is conjugated to a protein or protein domain that can translocate between the two cell portions.

Screen 6: Identification of Compounds that Suppress or Enhance Known Protein-Protein Binding Interactions. This screen is carried out with libraries of compounds of various types, as described above.

The foregoing embodiments presented in the detailed specification, drawings, and examples are illustrative of the present invention, and are not to be construed as limiting thereof. Modifications may be made from these embodiments without departing from the scope of the invention. The invention is defined by the following claims, with equivalents of the claims to be included therein.

What is claimed is:

1. An apparatus for screening for translocation of a first protein of interest in vivo in a cell, comprising:
   (a) a total internal reflection member having a surface portion, with
   (b) a cell contacted to said surface portion by the plasma membrane of said cell, said cell containing said first protein of interest, said protein of interest having a fluorescent group conjugated thereto;
   (c) a light source operatively associated with said total internal reflection member and positioned for directing a source light into said member to produce an evanescent field adjacent said surface portion, with said evanescent field extending into a first portion of said cell adjacent said plasma membrane, said evanescent field being weaker in a second portion of said cell, said fluorescent group emitting light when in said first portion of said cell and emitting less light when in said second portion of said cell; and (d) a light detector operatively associated with said total internal reflection member and configured to detect emitted light from said cell, whereby the emission of more or less light from said cell indicates the translocation of said protein between said first and second portions of said cell.

2. An apparatus according to claim 1, wherein said light source comprises a coherent light source.

3. An apparatus according to claim 1, wherein said total internal reflection member comprises a prism.

4. An apparatus according to claim 1, wherein said light detector comprises a CCD camera.

5. An apparatus according to claim 1 wherein said protein having said fluorescent group conjugated thereto is a first protein of interest, said cell further containing a second protein of interest located in either said first portion of said cell or said second portion of said cell, whereby the emission of more or less light from said cell indicates the presence or absence of specific binding between said first and second proteins of interest.

6. An apparatus according to claim 1, wherein said first and second proteins are members of a specific binding pair.

7. A method of detecting translocation of a first protein of interest within a cell, comprising:

(a) providing a total internal reflection member having a surface portion, with a cell contacted to said surface portion by the plasma membrane of said cell;

(b) directing a source light into said member to produce an evanescent field adjacent said surface portion, with said evanescent field extending into a first portion of said cell adjacent said plasma membrane, said evanescent field being weaker in a second portion of said cell; wherein said protein of interest has a fluorescent group conjugated thereto; said fluorescent group emitting light when in said first portion of said cell and emitting less light when in said second portion of said cell; and then (c) detecting emitted light from said fluorescent group, with the emission of more or less light from said fluorescent group indicating the translocation of said first protein of interest between said first and second portions of said cell.

8. A method according to claim 7, wherein said source light is coherent light.

9. A method according to claim 7, wherein said total internal reflection member comprises a prism.

10. A method according to claim 7, wherein said detecting step is carried out with a CCD camera.

11. A method according to claim 7, said cell further containing a second protein of interest, said second protein of interest located in either said first portion of said cell or said second portion of said cell, wherein the emission of more or less light from said fluorescent group indicates the presence or absence of specific binding between said first and second proteins of interest.

12. A method according to claim 11, wherein said first and second proteins of interest are members of a specific binding pair.

13. A method according to claim 11, further comprising the step of administering a test compound to said cell to determine whether or not said test compound disrupts the binding of said first and second proteins of interest.

14. A method according to claim 13, further comprising the step of repeating steps (a) through (c) at different concentrations of said test compound.

15. An apparatus for screening for translocation of a first protein of interest in vivo in a plurality of cells, comprising:

(a) a thin unitary total internal reflection member having a surface portion, with (b) a plurality cell contacted to said surface portion by the plasma membrane of said cell, said cell containing said first protein of interest, said protein of interest having a fluorescent group conjugated thereto;

(c) a light source operatively associated with said total internal reflection member and positioned for directing a source light into said member to produce an evanescent field adjacent said surface portion, with said evanescent field extending into a first portion of said cell adjacent said plasma membrane, said evanescent field being weaker in a second portion of said cell, said fluorescent group emitting light when in said first portion of said cell and emitting less light when in said second portion of said cell;

(d) coupling means for coupling said light source to said thin unitary total internal reflection member and illuminate at least 10 square millimeters of said surface portion; and (e) a light detector operatively associated with said total internal reflection member and configured to detect emitted light from said cells, whereby the emission of more or less light from said cell indicates the translocation of said protein between said first and second portions of said cell.

16. An apparatus according to claim 15, wherein said light source comprises a coherent light source.

17. An apparatus according to claim 15, wherein said total internal reflection member comprises a microscope coverslip.

18. An apparatus according to claim 15, wherein said light detector comprises a CCD camera.

19. An apparatus according to claim 15 wherein said protein having said fluorescent group conjugated thereto is a first protein of interest, said cell further containing a second protein of interest located in either said first portion of said cell or said second portion of said cell, whereby the emission of more or less light from said cell indicates the presence or absence of specific binding between said first and second proteins of interest.

20. An apparatus according to claim 15, wherein said first and second proteins are members of a specific binding pair.

21. A method of detecting translocation of a first protein of interest within a cell, comprising:

(a) providing a thin unitary total internal reflection member having a surface portion, with a cell contacted to said surface portion by the plasma membrane of said cell;

(b) directing a source light into said member through a coupling means to produce an evanescent field adjacent said surface portion in an area of at least 10 square millimeters, with said evanescent field extending into a first portion of said cell adjacent said plasma membrane, said evanescent field being weaker in a second portion of said cell; wherein said protein of interest has a fluorescent group conjugated thereto; said fluorescent group emitting light when in said first portion of said cell and emitting less light when in said second portion of said cell; and then (c) detecting emitted light from said fluorescent group, with the emission of more or less light from said fluorescent group indicating the translocation of said first protein of interest between said first and second portions of said cell.

22. A method according to claim 21, wherein said source light is coherent light.

23. A method according to claim 21, wherein said total internal reflection member comprises a prism.

24. A method according to claim 21, wherein said detecting step is carried out with a CCD camera.

25. A method according to claim 21, said cell further containing a second protein of interest, said second protein of interest located in either said first portion of said cell or said second portion of said cell, wherein the emission of more or less light from said fluorescent group indicates the presence or absence of specific binding between said first and second proteins of interest.

26. A method according to claim 24, wherein said first and second proteins of interest are members of a specific binding pair.

27. A method according to claim 24, further comprising the step of administering a test compound to said cell to determine whether or not said test compound disrupts the binding of said first and second proteins of interest.

28. A method according to claim 26, further comprising the step of repeating steps (a) through (c) at different concentrations of said test compound.

29. An apparatus according to claim 15, wherein said apparatus comprises an inverted wide-field microscope.

30. An apparatus according to claim 21, wherein said apparatus comprises an inverted wide-field microscope.

31. A method according to claim 28, wherein said thin unitary total internal reflection element is carried by an inverted wide-field microscope.

* * * * *

UNITED STATES PATENT AND TRADEMARK OFFICE
CERTIFICATE OF CORRECTION

PATENT NO.   : 6,682,927 B2
DATED        : January 27, 2004
INVENTOR(S)  : Meyer et al.

It is certified that error appears in the above-identified patent and that said Letters Patent is hereby corrected as shown below:

<u>Title page,</u>
Item [63], Related U.S. Application Data, should read -- Continuation-in-part No. PCT/WO00/20859, filed on Aug. 31, 1999. --

<u>Column 1,</u>
Line 11, should read -- PCT application PCT/WO00/20859, filed on Aug. 31, 1999 --

Signed and Sealed this

Tenth Day of August, 2004

JON W. DUDAS
*Acting Director of the United States Patent and Trademark Office*